United States Patent
Tao et al.

(10) Patent No.: US 9,909,993 B2
(45) Date of Patent: Mar. 6, 2018

(54) LABEL-FREE DETECTION OF SMALL AND LARGE MOLECULE INTERACTIONS, AND ACTIVITIES IN BIOLOGICAL SYSTEMS

(71) Applicants: Nongjian Tao, Fountain Hills, AZ (US); Yan Guan, Tempe, AZ (US)

(72) Inventors: Nongjian Tao, Fountain Hills, AZ (US); Yan Guan, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 136 days.

(21) Appl. No.: 14/968,331

(22) Filed: Dec. 14, 2015

(65) Prior Publication Data
US 2016/0169873 A1     Jun. 16, 2016

Related U.S. Application Data

(60) Provisional application No. 62/091,828, filed on Dec. 15, 2014.

(51) Int. Cl.
*G01N 33/50*   (2006.01)
*G01N 21/77*   (2006.01)
*G02B 21/36*   (2006.01)

(52) U.S. Cl.
CPC ......... *G01N 21/77* (2013.01); *G01N 33/5008* (2013.01); *G02B 21/365* (2013.01)

(58) Field of Classification Search
CPC ............. G06T 7/0012; G06T 7/20; G06T 2207/30004; G06T 2207/10056;
(Continued)

(56) References Cited

U.S. PATENT DOCUMENTS 5,471,458 A * 11/1995 Oguchi ............. G11B 9/14
                                              369/101
6,590,703 B2 * 7/2003 Park ................ B82Y 35/00
                                              359/368
(Continued)

OTHER PUBLICATIONS

Tran, Truong An, Jean Yves Le Guennec, Philippe Bougnoux, Francois Tranquart, and Ayache Bouakaz. "Characterization of cell membrane response to ultrasound activated microbubbles." IEEE transactions on ultrasonics, ferroelectrics, and frequency control 55, No. 1 (2008): 43-49.*

(Continued)

*Primary Examiner* — Sumati Lefkowitz
*Assistant Examiner* — Carol Wang
(74) *Attorney, Agent, or Firm* — George A. Leone; Citadel Patent Law

(57) ABSTRACT

A system for quantitative detection and analysis of the interactions of molecules with molecular receptors on the surfaces of biological cells based on detecting a mechanical deformation in the membrane of a cell associated with the molecular interactions, which works for both large and small molecules. The mechanical deformation can be detected with high precision in real time from an optical image of the cell with a differential detection method. The system can be also used to detect the electrical activities, such as ion channel opening and closing, as well as action potential propagation in neuronal cells.

23 Claims, 12 Drawing Sheets

(58) Field of Classification Search
CPC ...... G06T 2207/30024; G06T 2210/41; G06K
9/00127; G01N 2800/52; G01N 33/5008;
G01N 33/574; G01N 33/4833; G01N
33/5026; G01N 33/566; G01N 33/5058;
G01N 2015/1006; G01N 2015/1495;
G01N 2015/1497; G01N 2015/105; G01N
2500/10; G01N 2021/0325; G01N
2203/0647; G01N 2223/401; G01N
29/0654; G01N 21/77; G02B 21/365
See application file for complete search history.

(56) References Cited

U.S. PATENT DOCUMENTS

| | | | | |
|---|---|---|---|---|
| 6,678,416 | B1 * | 1/2004 | Sun | G06T 7/12 382/235 |
| 2005/0227350 | A1 * | 10/2005 | Muthiah | G01N 15/147 435/288.5 |
| 2008/0279441 | A1 * | 11/2008 | Matsuo | G01N 15/1475 382/133 |
| 2009/0208059 | A1 * | 8/2009 | Geva | G06K 9/3258 382/105 |
| 2010/0284016 | A1 * | 11/2010 | Teitell | G01J 3/453 356/451 |
| 2011/0287948 | A1 * | 11/2011 | Suresh | B01L 3/502746 506/7 |
| 2013/0089869 | A1 * | 4/2013 | Blobe | G01N 33/5044 435/7.1 |
| 2015/0285760 | A1 * | 10/2015 | Clyne | B03C 5/026 204/547 |

OTHER PUBLICATIONS

Pacheco, Mary A., Tina E. Pastoor, Ronald J. Lukas, and Lynn Wecker. "Characterization of human α4β2 neuronal nicotinic receptors stably expressed in SH-EP1 cells." Neurochemical research 26, No. 6 (2001): 683-693.*

Mailander, Volker, and Katharina Landfester. "Interaction of nanoparticles with cells." Biomacromolecules 10, No. 9 (2009): 2379-2400.* van Wamel, Annemieke, Ayache Bouakaz, Michel Versluis, and Nico de Jong. "Micromanipulation of endothelial cells: ultrasound-microbubble-cell interaction." Ultrasound in medicine & biology 30, No. 9 (2004): 1255-1258.*

Ehrlich, Address in Pathology on Chemotherapeutics: Scientific Principles, Methods, and Results., Lancet, Aug. 1913, 182(4694):445-451.

Copeland et al., Drug-target residence time and its implications for lead optimization., Nature Rev. Drug Disc., Sep. 2006, 5(9):730-739.

Swinney et al., The role of binding kinetics in therapeutically useful drug action., Curr. Opin. Drug Disc. Develop., Jan. 2009, 12(1):31-39.

Ernst et al., Determination of Equilibrium Dissociation Constants, Therapeutic Monoclonal Antibodies: From Bench to Clinic (ed. Zhiqiang An), Nov. 2009, 503-524, John Wiley & Sons, Hoboken, NJ.

Butcher, Can cell systems biology rescue drug discovery?, Nature Rev. Drug Disc., Jun. 2005, 4(6):461-467.

Hopkins et al., The druggable genome., Nature Rev. Drug Disc., Sep. 2002, 1(9):727-730.

Nahta et al., Herceptin: mechanisms of action and resistance., Cancer Lett., Feb. 2006, 232(2):123-138.

Nahta et al., Mechanisms of Disease: understanding resistance to HER2-targeted therapy in human breast cancer., Nat. Clin. Pract. Oncol., May 2006, 3(5):269-280.

Valabrega et al., Trastuzumab: mechanism of action, resistance and future perspectives in HER2-overexpressing breast cancer., Ann. Oncol., Jun. 2007, 18(6):977-984.

Nagy et al., Decreased accessibility and lack of activation of ErbB2 in JIMT-1, a herceptin-resistant, MUC4-expressing breast cancer cell line., Cancer Res., Jan. 2005, 65(2):473-482.

Price-Shiavi et al., Rat Muc4 (sialomucin complex) reduces binding of anti-ErbB2 antibodies to tumor cell surfaces, a potential mechanism for herceptin resistance., Int. J. Cancer., Jun. 2002, 99(6):783-791.

Kute et al., Development of Herceptin resistance in breast cancer cells., Cyto. Part A, Feb. 2004, 57A(2):86-93.

Lu et al., Insulin-Like Growth Factor-I Receptor Signaling and Resistance to Trastuzumab (Herceptin)., J. Natl. Cancer Inst., Dec. 2001, 93(24):1852-1857.

Natha et al., P27(kip1) down-regulation is associated with trastuzumab resistance in breast cancer cells., Cancer Res., Jun. 2004, 64:3981-3986.

Darling et al., Kinetic exclusion assay technology: characterization of molecular interactions., Assay Drug Develop. Technol., Dec. 2004, 2(6):647-657.

Xie et al., Measurement of the functional affinity constant of a monoclonal antibody for cell surface receptors using kinetic exclusion fluorescence immunoassay., J. Immuno. Methods, Sep. 2005, 304(1-2)1-14.

Rathanaswami et al., High-affinity binding measurements of antibodies to cell-surface-expressed antigens., Anal. Biochem., Feb. 2008, 373(1):52-60.

Pei et al., Real-time analysis of the carbohydrates on cell surfaces using a QCM biosensor: A lectin-based approach, Biosen. Bioelectron., May 2012, 35(1):200-205.

Wang et al., Label-free measuring and mapping of binding kinetics of membrane proteins in single living cells., Nature Chem., Oct. 2012, 4(10):846-853.

Troise et al., Differential binding of human immunoagents and Herceptin to the ErbB2 receptor., FEBS J., Oct. 2008, 275(20):4967-4979.

Pan et al., Molecular determinants of drug-receptor binding kinetics., Drug Disc. Today., Jul. 2013, 18(13-14):667-673.

Defazio-Eli et al., Quantitative assays for the measurement of HER1-HER2 heterodimerization and phosphorylation in cell lines and breast tumors: Applications for diagnostics and targeted drug mechanism of action., Breast Cancer Res., Apr. 2011, 13(2):R44.

Pearlberg et al., Screens using RNAi and cDNA expression as surrogates for genetics in mammalian tissue culture cells., Cold Spring Harb. Symp. Quant. Biol., 2005, 70(1):449-459.

Hathaway et al., Detection of breast cancer cells using targeted magnetic nanoparticles and ultra-sensitive magnetic field sensors., Breast Cancer Res., 2011, 13(15):R108.

Gineste et al., Three-dimensional automated nanoparticle tracking using Mie scattering in an optical microscope., J. Microsc., Aug. 2011, 243(2):172-178.

Guan et al., Kinetics of small molecule interactions with membrane proteins in single cells measured with mechanical amplification., Science Advances, Oct. 2015, 1(9):e1500633.

White et al., Biophysical dissection of membrane proteins., Nature, May 2006, 459(7245):344-346.

Changeux et al., 50 years of allosteric interactions: the twists and turns of the models., Nat. Rev. Mol. Cell. Biol., Dec. 2013, 14(12):819-829.

Almendro et al., Cellular heterogeneity and molecular evolution in cancer., Annu Rev Pathol., Jan. 2013, 8(1):277-302.

Meacham et al., Tumour heterogeneity and cancer cell plasticity., Nature, 2013, 501(7467):328-337.

Wu et al., Origin of Nanomechanical Cantilever Motion Generated from Biomolecular Interactions., Proc. Natl. Acad. Sci. USA, Feb. 2001, 98(4):1560-1564.

Cross et al., Nanomechanical analysis of cells from cancer patients., Nat. Nanotechnol., Dec. 2007, 2(12):780-783.

Lulevich et al., Single-cell mechanics provides a sensitive and quantitative means for probing amyloid-β peptide and neuronal cell interactions., Proc. Natl. Acad. Sci. USA, Aug. 2010, 107(31)13872-13877.

Guan et al., Detection of molecular binding via charge-induced mechanical response of optical fibers., Chem. Sci., 2014, 5(11):4375-4381.

(56) References Cited

OTHER PUBLICATIONS

Dell et al., Glycoprotein Structure Determination by Mass Spectrometry., Science, Mar. 2001, 291(5512):2351-2356.
Schuller, Is cancer triggered by altered signalling of nicotinic acetylcholine receptors?, Nat. Rev. Cancer, Mar. 2009, 9(3):195-205.
Taly et al., Nicotinic receptors: allosteric transitions and therapeutic targets in the nervous system, Nat. Rev. Drug. Discov., Sep. 2009, 8(9):733-750.
Albuquerque et al., Mammalian Nicotinic Acetylcholine Receptors: From Structure to Function., Physiol. rev., Jan. 2009, 89(1):73-120.
Eaton et al., Characterization of human alpha 4 beta 2-nicotinic acetylcholine receptors stably and heterologously expressed in native nicotinic receptor-null SH-EP1 human epithelial cells., Mol. Pharmacol., Dec. 2003, 64(6):1283-1294.
Jensen et al., Carbamoylcholine homologs: Novel and potent agonists at neuronal nicotinic acetylcholine receptors., Mol. Pharmacol., Oct. 2003, 64(4):865-875.
Concepcion et al., Label-free detection of biomolecular interactions using BioLayer Interferometry for kinetic characterization., Comb Chem High Throughput Screen., Sep. 2009, 12(8):791-800.
Bornhop et al., Free-Solution, Label-Free Molecular Interactions Studied by Back-Scattering Interferometry., Science, Sep. 2007, 317(5845):1732-1736.
Eaton et al., Correction to Characterization of human α4β2-nicotinic acetylcholine receptors stably and heterologously expressed in native nicotinic receptor-null SH-EP1 human epithelial cells, Mol. Pharmacol., Jul. 2004, 66(1):197.
Puchtler et al., On the chemistry of formaldehyde fixation and its effects on immunohistochemical reactions, Histochemistry, 1985, 82(3):201-204.
Dapson, Macromolecular changes caused by formalin fixation and antigen retrieval., Biotech. Histochem., Jun. 2007, 32(3):133-140.
Wang et al., Automated electrophysiology: high throughput of art., Assay. Drug Dev. Technol., Oct. 2003, 1(5):695-708.
Dunlop et al., High-throughput electrophysiology: an emerging paradigm for ion-channel screening and physiology., Vat. Rev. Drug Discov., Apr. 2008, 7(4):358-368.
Griffiths et al., Density of Newly Synthesized Plasma Membrane Proteins in Intracellular Membranes. I. Stereological Studies., J. Cell. Biol., Jun. 1984, 98(6):2133-2141.
Quinn et al., Density of Newly Synthesized Plasma Membrane Proteins in Intracellular Membranes II. Biochemical Studies., J. Cell. Biol., Jun. 1984, 98(6):2142-2147.
Paganin et al., Noninterferometric phase imaging with partially coherent light., Phys. Rev. Lett., Mar. 1998, 80(12):2586-2589.
Mendelsohn et al., The EGF receptor family as targets for cancer therapy,. Oncogene, Dec. 2000, 19(56):6550-6565.
Nicholson et al., EGFR and cancer prognosis., Eur. J. Cancer, Sep. 2001, 37(supp. 4):9-15.
Press et al., EGFR, HER2 and VEGF pathways: validated targets for cancer treatment., Drugs, 67(14):2045-2075.
Johnston et al., Targeting the EGFR pathway for cancer therapy., Curr. Med. Chem., 2006, 13(29):3483-92.
Arteaga, Epidermal growth factor receptor dependence in human tumors: more than just expression?, Oncologist, Aug. 2002, 7(supp. 4):31-39.
Herbst et al., IMC-C225, an anti-epidermal growth factor receptor monoclonal antibody for treatment of head and neck cancer., Semin. Oncol., Oct. 2002, 29(5):18-30.
Adams et al., Monoclonal antibody therapy of cancer., Nat. Biotechnol., Sep. 2005, 23(9):1147-1157.
Herbst et al., Monoclonal antibodies to target epidermal growth factor receptor-positive tumors a new paradigm for cancer therapy., Cancer, Mar. 2002, 94(5):1593-1611.
Legros et al., Generating a High Affinity Scorpion Toxin Receptor in KcsA-Kv1.3 Chimeric Potassium Channels., J. Biol. Chem., Jun. 2000, 275(22):16918-16924.
Nguyen et al., Use of Kv1.3 Blockers for Inflammatory Skin Conditions., Curr. Med. Chem., 2010, 17(26):2882-2896.
Thurmond et al., The role of histamine H1 and H4 receptors in allergic inflammation: The search for new antihistamines., Nat. Rev. Drug. Dicov., Jan. 2008, 7(1):41-53.
Molek et al., Peptide phage display as a tool for drug discovery: Targeting membrane receptors., Molecules, Jan. 2011, 16(1):857-887.
Im et al., Membrane protein biosensing with plasmonic nanopore arrays and pore-spanning lipid membranes., Chem. Sci., Dec. 2010, 1(6):688-696.
Maynard et al., Surface plasmon resonance for high-throughput ligand screening of membrane-bound proteins., Biotechnol. J., Nov. 2009, 4(11):1542-1558.
Zhang et al., Optical tweezers for single cells., J. R. Soc. Interface., Jul. 2008, 5(24):671-690.
Bambardekar et al., Direct laser manipulation reveals the mechanics of cell contacts in vivo., Proc. Natl. Acad. Sci. USA., Feb. 2015, 112(5):1416-1421.
Park et al., Measurement of red blood cell mechanics during morphological changes., Proc. Natl. Acad. Sci. USA., Apr. 2010, 107(15):6731-6736.
Park et al., Metabolic Remodeling of the Human Red Blood Cell Membrane., Proc. Natl. Acad. Sci. USA., Jan. 2010, 107(4):1289-1294.
Tao et al., High resolution surface plasmon resonance spectroscopy., Rev. Sci. Instrum., Dec. 1999, 70(12):4656-4660.
Shan et al., Imaging Local Electrochemical Current via Surface Plasmon Resonance., Science, Mar. 2010, 327(5971):1363-1366.
Smith et al., Effect of Wheat Germ Agglutinin on the Viscoelastic Properties of Erythrocyte Membrane., J. Cell. Biol., Jul. 1982, 94(1):7-11.
Evans et al., Adhesivity and rigidity of erythrocyte membrane in relation to wheat germ agglutinin binding., J. Cell. Biol., Apr. 1984, 98(4): 1201-1208.
Lu et al., Plasmonic-based electrochemical impedance spectroscopy: application to molecular binding., Anal. Chem., Jan. 2012, 84(1):327-333.
Shan et al., Detection of Charges and Molecules with Self-Assembled Nano-Oscillators., Nano. Letters, Jul. 2014, 14(7):4151-4157.
Eaton et al., Correction to "Characterization of human α4β2-nicotinic acetylcholine receptors stably and heterologously expressed in native nicotinic receptor-null SH-EP1 human epithelial cells.," Mol. Pharmacol., Jul. 2004, 66:197-197.
Anker et al., Biosensing with plasmonic nanosensors., Nat. Meter., Jun. 2008, 7( 6):442-453.
Ebbesen et al., Extraordinary optical transmission through sub-wavelength hole arrays., Nature, Feb. 1998, 391(6668):667-669.
Helfrich et al., Elastic Properties of Lipid Bilayers: Theory and Possible Experiments., Z. Naturforsch. C., Nov.-Dec. 1973, 28(11):693-703.
Leibler, Curvature instability in membranes., Journal de Physique., 1986, 47(3):507-516.
Zimmerberg et al., How proteins produce cellular membrane curvature., Nat. Rev. Mol. Cell Biol., Jan. 2006, 7(1):9-19.
McMahon et al., Membrane curvature at a glance., J. Cell Sci., Mar. 2015, 128(6):1065-1070.
Callan-Jones et al., Curvature-driven membrane lipid and protein distribution., Curr. Opin. Solid St ate Mater. Sci., Aug. 2013, 17(4):143-150.
Vallejo et al., Chronic Nicotine Exposure Upregulates Nicotinic Receptors by a Novel Mechanism., J. Neurosci., Jun. 2005, 25(23):5563-5572.
Chabot et al., Biosensing based on surface plasmon resonance and living cells., Biosens. Bioelectron., Feb. 2009, 24(6):1667-1673.
Zhou et al., Impact of intrinsic affinity on functional binding and biological activity of EGFR antibodies., Mol. Cancer Ther., Jul. 2012, 11(7):1467-1476.

\* cited by examiner

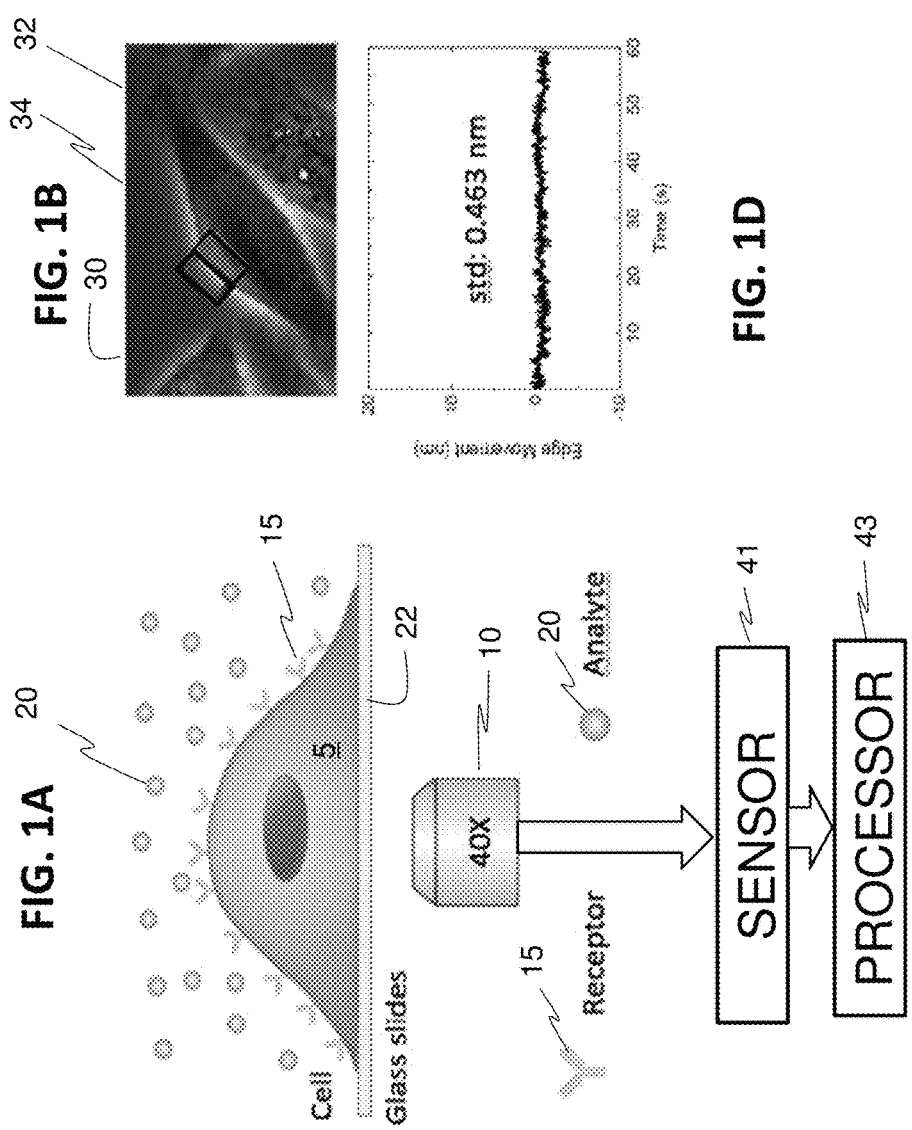

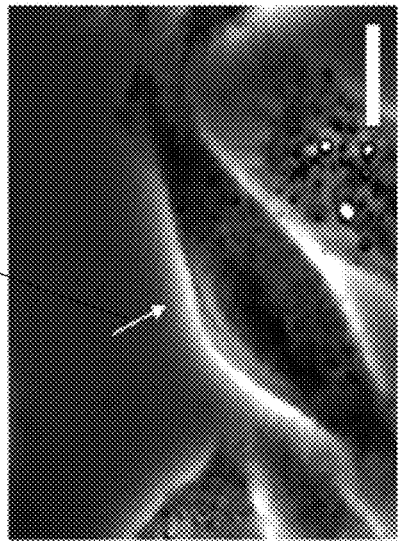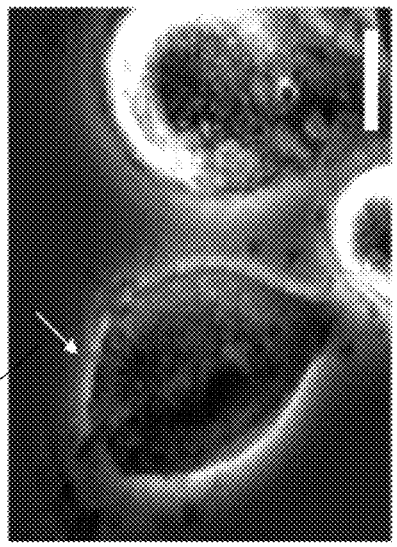
FIG. 2B
FIG. 2A
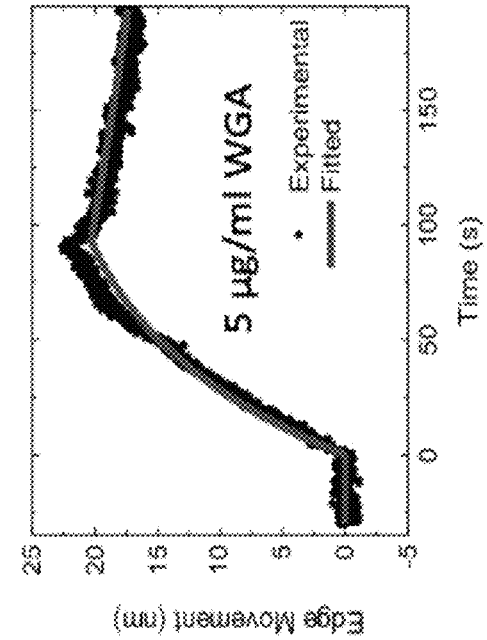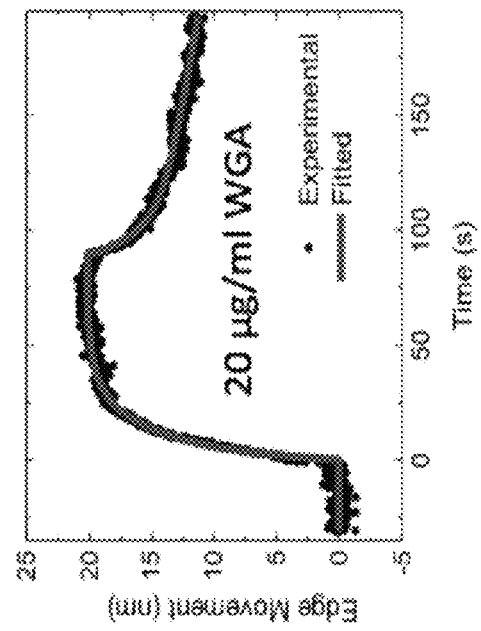
FIG. 2D
FIG. 2C

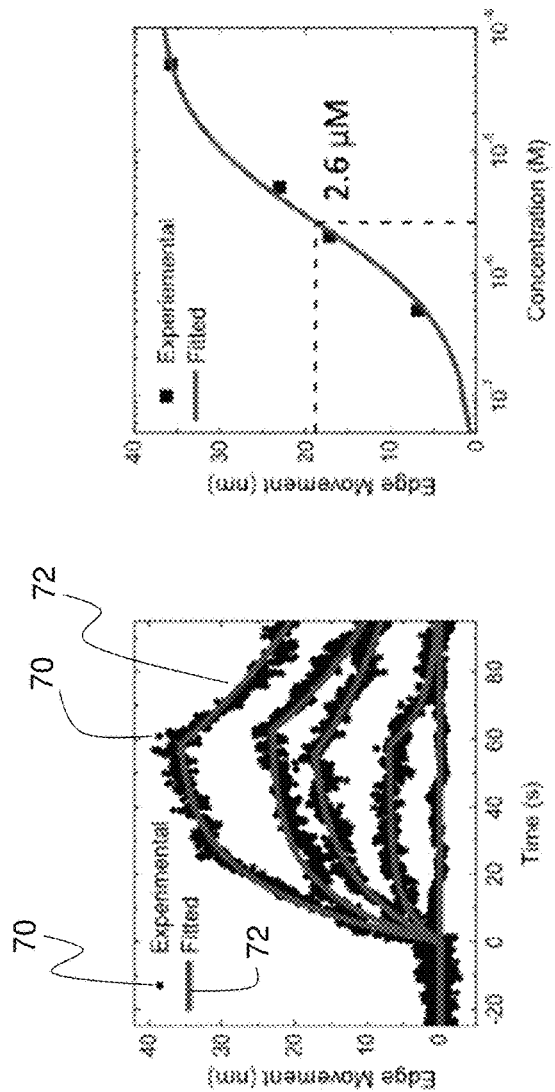

LABEL-FREE DETECTION OF SMALL AND LARGE MOLECULE INTERACTIONS, AND ACTIVITIES IN BIOLOGICAL SYSTEMS

CROSS-REFERENCE TO RELATED APPLICATION

This application is a non-provisional application of U.S. Provisional Patent Application No. 62/091,828, filed Dec. 15, 2014, entitled "LABEL-FREE DETECTION OF SMALL AND LARGE MOLECULE INTERACTIONS, AND ACTIVITIES IN BIOLOGICAL SYSTEMS," to the same inventors herein and claims the priority benefit of that filing date. Application No. 62/091,828 is incorporated by reference.

TECHNICAL FIELD

The present invention relates to the field of biomedical research, screening and development of drugs, and discovery, validation and detection of biomarkers for diseases, and, more particularly, to a method based on nanometer-precision tracking of molecular binding-induced mechanical deformation in the cell membrane via optical imaging, which is label-free, real time and non-invasive.

BACKGROUND

Measuring molecular binding or interactions is a basic task for understanding many biological processes and for developing relevant applications. A particularly important application is to determine the binding properties of drugs with their corresponding membrane protein receptors, which are the largest type of drug targets.[1] Molecular binding is quantified by kinetic constants, which have, thus, become a criterion in preclinical drug screening.[2,3]

Advances in structural biology have led to an exponential growth in the number of membrane proteins with determined 3D structures. However, as noted above, in order to understand the cellular functions of membrane proteins, it is also necessary to determine the interaction kinetics of the membrane proteins with various molecules. This is because cells perform many functions, including communication, via the interactions of their membrane proteins with molecules in the extracellular medium. A capability to quantify membrane protein interactions with molecules is also critical for discovering and validating drugs because most drug targets are membrane proteins. Despite the importance, developing such a capability that can measure the interactions of molecules with membrane proteins in the natural lipid environment has been a difficult task.

One traditional method for determining the kinetic constants is to extract molecular receptors from cells, immobilize them on a solid surface after purification, and then expose them to the drug for binding.[4] Although useful, such methods can be problematic, especially when the receptors are membrane proteins,[5] which currently count for more than a half of the drug targets.[6] Due to their unique amphiphilic structures, it is difficult to ensure that the purified membrane proteins retain their native structures and functions.[4] Because of the heterogeneous nature of cells, it is also important to study each of the individual cells. These capabilities, if developed, will benefit not only drug discovery, but also drug resistance study, which is a common but difficult problem in medicine.[7-9]

Typically, methods for studying molecular interactions use radioactive or fluorescent labels. These end point assays do not provide kinetic constants that are needed to quantify the membrane interactions and functions. To determine the kinetic information, the current practice involves extracting membrane proteins from cells, purifying them from the extracts, immobilizing the purified proteins on a solid surface, and then exposing them to a ligand for kinetic study. The procedures are not only laborious, but also prone to alteration of the native functions of membrane proteins, especially integral membrane proteins that are permanently attached to the membrane. Furthermore, the isolation of membrane proteins from their native cellular environment prevents one from studying the allosteric effect in the molecular interactions, and examining heterogeneous nature of cells. A more serious limitation of the existing technologies is that the detection signal diminishes with the mass of the molecule, making them difficult for detecting small molecules, which play many important roles in cellular functions, and represent the vast majority of the existing drugs.

Various methods have been developed for in situ measurement of drug-receptor binding. A popular method is kinetic exclusion assay, which measures the concentration of free drugs remaining in the supernatant after the binding equilibrium in cell suspension is achieved with a labeled detection technology.[15-17] This is an end-point assay, and not suitable for extracting the kinetic constants, including the association and dissociation constants. Furthermore, the use of labels is not only labor intensive but may also affect the native binding behaviors of the molecular receptors. Label-free technologies, such as quartz crystal microbalance, have been developed for studying drug binding properties.[18] Although useful, they lack spatial resolution required to study the variability between different individual cells, map heterogeneous distribution of receptors in the cell membrane, and distinguish non-specific binding onto the sensor surface from specific binding to the receptors on the cells. Another label-free detection technology is surface plasmon resonance (SPR) technique that can monitor the lectingly-coprotein interactions in single cells.[19] However, like the quartz crystal microbalance, SPR signal is proportional to the mass of the molecule (e.g., drug), which has limited sensitivity for detecting drug molecules with typically small molecular masses.

The present invention overcomes the shortcomings discussed above and, for the first time, discloses a system that can detect the binding of both large and small molecules with the molecular receptors in single cells, and analyze the corresponding binding kinetic constants. The method can be applied to measure the binding of drugs with their membrane receptor targets in the native cellular membranes, and to analyze cell-to-cell variability of the binding kinetics by measuring mechanical deformation of cells upon interactions of the cellular membrane proteins with molecules in the extracellular medium. A capability of real time analysis of the interactions in single cells by analyzing the mechanical deformation with sub-nm resolution is also provided for the first time. For small molecules, the present method represents the first kinetic measurement while the equilibrium constants extracted from the present method are consistent with those obtained with endpoint radioactive labeling assay. The imaging capability allows revelation of cell-to-cell variability of difference cells, and region-to-region variability within the same cell. The detection principle of the present invention may also be used to monitor the electrical activities in neurons.

BRIEF SUMMARY OF THE DISCLOSURE

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A system for quantitative detection and analysis of the interactions of molecules with molecular receptors on the surfaces of biological cells based on detecting a mechanical deformation in the membrane of a cell associated with the molecular interactions is disclosed. An imaging apparatus captures a time sequence of images of a biological object includes an injector coupled to introduce a substance that interacts with the biological object. A processor is coupled to receive data from the imaging apparatus and adapted to determine the mechanical deformation of the biological object associated with the interaction of the substance with the biological object from the images, the processor being further adapted to analyze the interaction from the mechanical deformation.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 1A schematically shows illumination of the setup for edge tracking detection.

FIG. 1B illustrates differential optical detection for accurate tracking of cell edge change induced by analyte receptor interaction.

FIG. 1C graphically illustrates a typical binding curve as determined from the cell edge movement.

FIG. 1D graphically illustrates an example where the root mean square of the fixed cell edge change is about 0.46 nm.

FIG. 1E is a cartoon that illustrates cell edge changes over time during the binding process. i, ii, and iii correspond to the stages marked in FIG. 1C.

FIG. 2A shows WGA interaction with glycoproteins featuring phase contrast images of fixed CP-D cells for 20 g/ml WGA binding.

FIG. 2B shows WGA interaction with glycoproteins featuring phase contrast images of fixed CP-D cells for 5 g/ml WGA binding.

FIG. 2C graphically illustrates an example for averaged cell edge movement over the whole cell for 20 g/ml WGA.

FIG. 2D graphically illustrates an example for averaged cell edge movement over the whole cell for 5 g/ml WGA.

FIG. 3A shows acetylcholine interaction with nicotinic acetylcholine receptors in cells, specifically a phase contrast image of the fixed human a4β2 transfected SH-EP1 cells, where the white arrow marks the cell under analysis.

FIG. 3B shows averaged cell edge movement over the whole cell and fitting results during the binding process for acetylcholine of different concentrations.

FIG. 3C graphically illustrates an example wherein the equilibrium constant ($K_D$) was determined to be 2.601 µM by plotting the edge movement vs. acetylcholine concentration and fitting the data with the Langmuir isotherm.

Figures 3D, 3E, 3F:
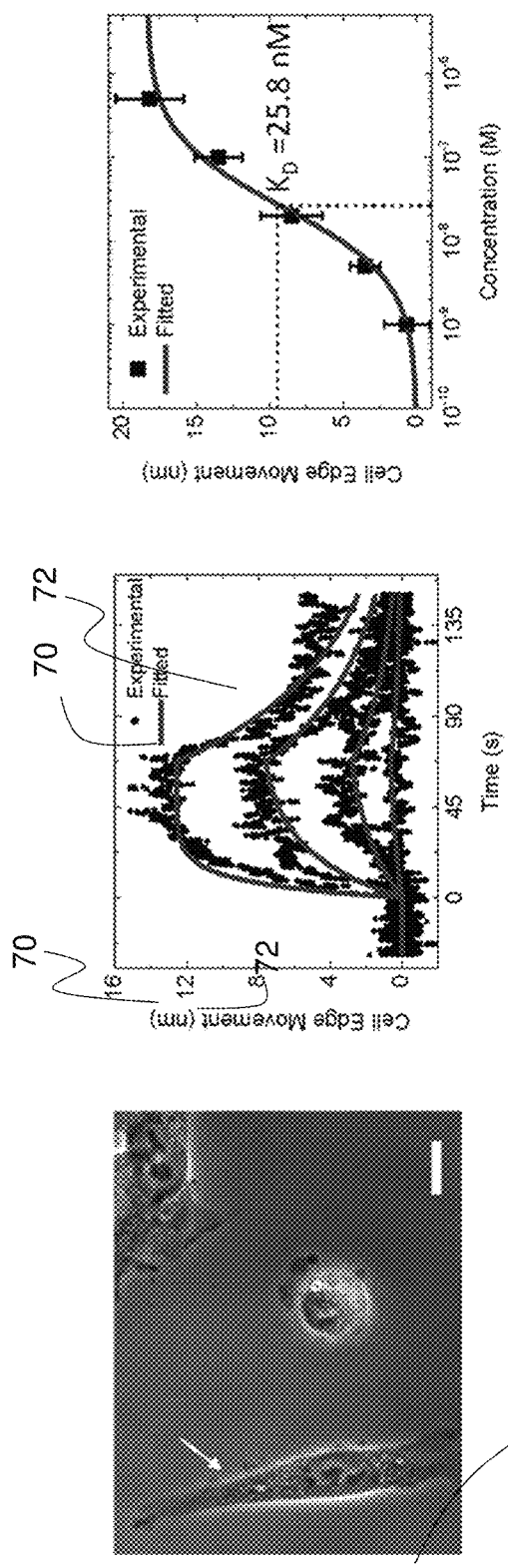
FIG. 3D shows acetylcholine interaction with nicotinic acetylcholine receptors in cells, specifically a phase contrast image of the fixed human a4β2 transfected SH-EP1 cells, where the white arrow marks the cell under analysis.
FIG. 3E shows averaged cell edge movement over the whole cell and fitting results during the binding process for acetylcholine of different concentrations.
FIG. 3F graphically illustrates an example wherein the equilibrium constant ($K_D$) was determined to be ~26 nM by plotting the edge movement vs. acetylcholine concentration and fitting the data with the Langmuir isotherm.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments for metabolic analyzers that are based on detection of several metabolic signatures. Several features of methods and systems in accordance with example embodiments are set forth and described in the figures. It will be appreciated that methods and systems in accordance with other example embodiments can include additional procedures or features different than those shown in the figures. Example embodiments are described herein with respect to a portable metabolic analyzer system. However, it will be understood that these examples are for the purpose of illustrating the principles, and that the invention is not so limited. Additionally, methods and systems in accordance with several example embodiments may not include all of the features shown in the figures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of sample collection or analysis:

As used herein, "plurality" is understood to mean more than one. For example, a plurality refers to at least 3, 4, 5, 70, or more.

As used herein, "neuron" refers to a nerve cell that receives and sends electrical signals over long distances within the body. A neuron receives electrical input signals from sensory cells (called sensory neurons) and from other neurons. The neuron sends electrical output signals to muscle neurons (called motoneurons or motor neurons) and to other neurons.

As used herein, "MADMI" refers to a method for mechanically amplified detection of molecular interactions that provides amplified molecular interaction signals, allowing measurement of the binding kinetics of molecules with membrane proteins on single live cells, and analysis of the heterogeneous nature of the binding kinetics between different cells, and different regions of a single cell.

As used herein, "Nicotinic acetylcholine receptors," or "nAChRs," are neuron receptor proteins that signal for muscular contraction upon a chemical stimulus.

Principle of the Invention

The basic detection principle of the present invention is to measure a deformation (shape or size) in the cell that accompanies the binding of molecules with the molecular receptors on the cell surface. This deformation occurs because the law of thermodynamics predicts that when molecules bind to the surface the surface tension changes. According to thermodynamics, the relative surface concentration of molecules bound on the membrane surface is given by $$\Gamma = -\left(\frac{\delta \Upsilon}{\delta \mu}\right)_{T,P}, \quad (1)$$

where $\gamma$ is the surface tension and $\mu$ is the chemical potential of the molecules. For ideal solutions, the chemical potential is related to the bulk concentration, c, according to $$d\mu = k_B T d\Gamma(\ln c), \quad (2)$$

where $k_B$ is the Boltzmann constant, and T is temperature. Substituting Eq. 2 into Eq. 1, we have $$d\gamma = kBTd\Gamma(dc/c), \quad (3)$$

If we assume the molecular binding follows the Langmuir isotherm, Eq. 3 can be simplified as $$d\gamma = RT\left(\frac{\Gamma_0}{\Gamma_0 - \Gamma}\right), \quad (4)$$

where $\Gamma_0$ is the surface concentration at the full (maximum) coverage. When $\Gamma \ll \Gamma_0$, Eq. 4 can be further simplified and takes the form of, $$d\gamma = k_B T d\Gamma. \quad (5)$$

Eq. 5 clearly shows that the surface tension of the cell membrane changes with the molecular binding.

Some of the receptor proteins are ion channels, which open and close to allow different ions to move in and out of a cell. Associated with the ion re-distribution is an electrical potential change across the cell's membrane, particularly neurons, giving rise to electrical activity, such as action potential that is critical for information processing in brains. The change in the ion distribution or electrical activities also leads to a mechanical deformation in the cell, as described the Lippmann equation, given by $$q = \left(\frac{\delta \Upsilon}{\delta V}\right)_{T,P,\mu}, \quad (6)$$

where q is surface charge density and V is the electrical potential. Eq. 6 predicts that for a given charge density, a change in the electrical potential results in a change in the surface tension, thus a mechanical deformation in the cell. This is the principle for the detection of electrical activities of neurons, such as action potential, by measuring and analyzing the cell deformation.

Note that Eq. 5 was derived with many assumptions, but the basic concept that a molecular binding event causes a change in the surface tension is expected to be a general phenomenon. However, the actual amount of conformational change in the cell depends on the biding strengths, as well as the geometry and mechanical properties of the cells. For practical applications, one typically wants to determine the binding kinetic constants, which can be obtained from the time dependence of the cell membrane deformation (mechanical response) during the association (binding) and dissociation (unbinding) processes. In other words, there is no need to relate the measured mechanical response to the microscopic scaled processes.

Description of the System

Referring now jointly to FIG. 1A-FIG. 1E, an overview of edge tracking detection employing the methods disclosed herein is illustrated. To detect a small amount of molecules or a weak molecular binding event, it is critical to be able to measure a small amount of mechanical deformation in the cell. This task is accomplished in the present system by detecting and tracking the edge movement of a cell image.

Referring now particularly to FIG. 1A, there shown schematically is an example of an illumination setup. The setup includes a cell 5 with receptors 15 on a glass slide 22. Analytes 20 are introduced and a differential interference contrast (DIC) microscope 10 is positioned to track activity. A traditional bright field optical microscopy may be used, but better image contrast can be obtained with phase contrast microscopy, differential interference contrast (DIC) microscopy, and various interference optical microscopic techniques. In one useful example an inverted phase contrast microscope with 40× phase 2 objective 10 was used for detection. The DIC microscope 10 transmits time sequenced images to a sensor 41, which in turn passes data representing the time sequenced images to a processor 43 for analysis. The sensor 41 may be any commercially available device such as a CCD video camera or equivalent. The processor may advantageously include a CPU or equivalent device for processing digital data, for example. The data for time sequenced images may be analyzed to determine differences in the edge boundaries for the cell at different times in response to analytes. Edge boundary measurement with software programs is well known. Using the microscope in combination with the sensor and processor detecting a mechanical deformation in the membrane of a cell associated with the molecular interactions can be performed as desired.

Referring now particularly to FIG. 1B, differential optical detection for accurate tracking of cell edge change induced by analyte receptor interaction is illustrated. The edge of a cell 5 can be manually defined from the optical image of the cell, but an imaging processing algorithm can automatically detect the cell edge, providing high throughput. After determining the cell edge, a region of interest (ROI) is selected at a location of the cell edge. The ROI can be a rectangular shape 30 with the cell edge 32 passing through the center portion of the rectangle, dividing the rectangle into two equal halves, one half 34 is inside of the cell, and the second half 36 falls outside of the cell. We denote the intensities of the two halves of the differential image as A and B, and (A−B)/(A+B) is calculated and used to determine the movement of the cell edge at each location. We refer (A−B)/(A+B) to as differential image intensity, and this method of edge movement tracking differential optical detection.

An alternative approach is to first determine a differential image within the ROI by shifting the image within the ROI perpendicular to the cell edge by a small distance (e.g., 1 pixel), and then calculating the difference between the shifted image and the original image pixel by pixel. We denote the intensities of the two halves of the differential image as dA and dB, and (dA−dB)/(dA+dB) is calculated and used to determine the movement of the cell edge at a given location. This method of edge movement tracking is also referred to as differential optical detection.

The relation between the cell edge movement and the measured differential image intensity change from one of the above differential optical detection method can be determined as below. The pixel density of each image is enlarged 5 times by adding additional pixels with a bilinear interpolation approach. The distance between two pixels in the interpolated image corresponds to a real distance of the object (cell) is 37 nm (Pike F032B CCD, Allied Vision Technologies, Stadtroda, Germany). The edge of one cell is manually chosen and the centroid (O) of the cell is determined (FIGS. 1B and 1C). A polar coordinate system is setup with the centroid serving as the pole. The cell edge movement was calculated at every 10 starting from 0 (FIG. 1E). The ROI at a certain point of the cell edge (point A) is then shifted by different numbers of pixels outwards (perpendicular to the tangential line at point A), and the corresponding changes in the differential image intensity is determined from the image. The relation between the differential image intensity and the cell edge movement (pixels) is found to be linear within a certain range, which serves as a calibration curve to determine the cell edge movement (mechanical deformation) from the differential image intensity. This differential optical detection method can accurately detect cell edge movement with a detection limit as small as 0.5 nm, the size of an atom (FIG. 1D).

Examples

Referring now jointly to FIG. 2A-FIG. 2D, there shown are illustrative drawings of WGA interaction with glycoproteins. White arrows 40, 42 mark the cells under analysis in FIG. 2A and FIG. 2B respectively. The scale bar for FIGS. 2C and 2D is 10 μm. FIG. 2C graphically illustrates an example for averaged cell edge movement over the whole cell for 20 g/ml WGA. FIG. 2D graphically illustrates an example for averaged cell edge movement over the whole cell for 5 g/ml WGA. The scale bar for FIGS. 2C and 2D is 10 μm. The Y axis for FIGS. 2C and 2D represents edge movement in nm ranging from −5 to 25 nm. The X axis represents time in seconds.

The following examples demonstrate the detection of the binding of both large and small molecules with membrane receptors in cells using the system and method in this system. An inverted microscope (Olympus X81) equipped with phase 2 condenser and phase 2 40× objective was used with illumination from the top of the sample cells.

Large Molecule-Membrane Receptor Protein Interactions

To demonstrate the capability of the system and method for detecting and analyzing molecular binding of membrane receptors of cells, the binding kinetics of wheat germ agglutinin (WGA) and glycoprotein on Barrett's esophagus derived CP-D (CP-18821) cells was studied. WGA is one kind of lectins that binds to N-Acetyl glucosamine (GlcNAc) and sialic acid groups. The CPD cells were fully attached onto a glass slide.

FIGS. 2A and 2B show the phase contrast images of attached fixed CP-D cells. The measurement was carried out by flowing 1×PBS over the cells for 30 s with a flow rate of 350 L/min to obtain the baseline. At time 0 s, WGA solution in 1×PBS was introduced for 90 s allowing the association (binding) of WGA with CP-D glycoprotein on the cell surface. During the association process, the cell edge moves outwards as shown in FIGS. 2C and 2D. Then WGA solution was switched to 1×PBS to allow the bound WGA to dissociate from the CP-D cells at time 90 s. FIGS. 2C and 2D show that the cell edge moves back to the original position during the dissociation process. By fitting the data with the first order kinetics, association rate constants ($k_{on}$), dissociation rate constants ($k_{off}$), and dissociation constant ($K_D$) were found to be
$k_{on}$=1.4×10$^5$ M$^{-1}$ s$^{-1}$, $k_{off}$=2.9×10$^{-3}$ s$^{-1}$, $K_D$=0.021 µM for 20 ug/ml WGA and $k_{on}$=1.09×10$^5$ M$^{-1}$ s$^{-1}$, $k_{off}$=1.56×10$^{-3}$ s$^{-1}$, $K_D$=0.014 µM for 5 ug/ml WGA.

Small Molecule-Membrane Receptor Protein Interactions

In order to demonstrate small molecule binding to single cells with the present system, the binding of acetylcholine with nicotinic acetylcholine receptors (nAChRs) was studied. Engineered SH-EP1 cells that expressed human α4β2 receptors were used to examine the binding kinetics of acetycholine with nAChRs. Human α4β2 mainly exists in the brain and is related to the nicotine addiction. Study of the nAChRs and small molecule interactions is important for revealing the mechanism of nicotine addiction as well as development of drugs to treat nicotine addiction.

Referring now jointly to FIG. 3A-FIG. 3C, acetylcholine interaction with nicotinic acetylcholine receptors in cells, specifically a phase contrast image of the fixed human a4β2 transfected SH-EP1 cells. The phase contrast image of fixed SH-EP1-hα4β2 cells is shown in FIG. 3A, where the white arrow 50 marks the cell under analysis. The scale bar is 10 µm.

1×PBS buffer was continuously flowing over the cell for 25 seconds to obtain a stable baseline. At time 0 s, the buffer was changed to acetylcholine solution of different concentrations in 1×PBS. After association, the acetylcholine solution was switched back to 1×PBS to allow dissociation.

Referring now particularly to FIG. 3B averaged cell edge movement over the whole cell and fitting results during the binding process for acetylcholine of different concentrations is shown. The Y axis represents edge movement in nm ranging from about 0 to 40 nm. The X axis represents time in seconds. Averaged cell edge movement over the whole cell is indicated by the experimental data points 70 fitted results are shown as a plurality of curves 72. From bottom to top the buffer (negative control), was 0.5 µM, 2 µM, 5 µM, and 50 µM.

As shown in FIG. 3B, the cell edge moves outwards during the association phase and retracts back during the dissociation phase. It also shows that the amount of cell edge movement during the association process increases with the acetylcholine concentration, which is expected for first-order reaction kinetics. The association rate constant ($k_{on}$) and dissociation rate constant ($k_{off}$) were found to be 9.4×10$^3$ M$^{-1}$ s$^{-1.4}$ nd 2.47×10$^{-2}$ s$^{-1}$ respectively, from which the dissociation constant ($K_D$) was determined to be 2.7 µM.

Referring now particularly to FIG. 3C, there illustrated is an example wherein the equilibrium constant ($K_D$) was determined to be 2.601 µM by plotting the edge movement vs. acetylcholine concentration and fitting the data with the Langmuir isotherm. The Y axis represents edge movement in nm ranging from about 0 to 40 nm. The X axis represents concentration (M) ranging from about 10$^{-7}$ to 10$^{-4}$ M.

Referring now jointly to FIG. 3D-FIG. 3F, acetylcholine interaction with nicotinic acetylcholine receptors in cells, specifically a phase contrast image of the fixed human a4β2 transfected SH-EP1 cells. The phase contrast image of fixed SH-EP1-hα4β2 cells is shown in FIG. 3D, where the white arrow 350 marks the cell under analysis. The scale bar is 20 µm. 1×PBS buffer was first introduced to flow over the cell for 25 s, and then the buffer was switched to an acetylcholine solution in 1×PBS. After association, the acetylcholine solution at each concentration was switched back to 1×PBS to allow for dissociation. The above procedure was repeated for different acetylcholine concentrations.

As shown in FIG. 3E, the cell edge expands during the association phase and retracts during the dissociation phase. FIG. 3E also shows that the amount of cell expansion during the association process increases with the acetylcholine concentration, which is expected for first-order binding kinetics. The association (kon) and dissociation (koff) rate constants were found to be 1.2×10$^{-6}$ M$^{-1}$ s$^{-1}$ and 2.2×10$^{-2}$ s$^{-1}$, respectively, which represent the first direct measurement of the kinetic constants for the binding of the neurotransmitter to the nAChRs in intact cells. From kon and koff, the equilibrium dissociation constant (KD=koff/kon) was determined to be 18.1 nM. By plotting the equilibrium response versus acetylcholine concentrations (FIG. 3F), the equilibrium constant (KD) was found to be ~26 nM, which is consistent with that obtained by kinetics measurement. As this is the first kinetic measurement of acetylcholine binding to nAChRs, the findings cannot be compared to other reference technologies or prior data. However, the equilibrium dissociation constant determined here is in good agreement with the average Ki determined with radioligand binding assay, which involved centrifuge and formation of cell pellets.

Figure 3H:
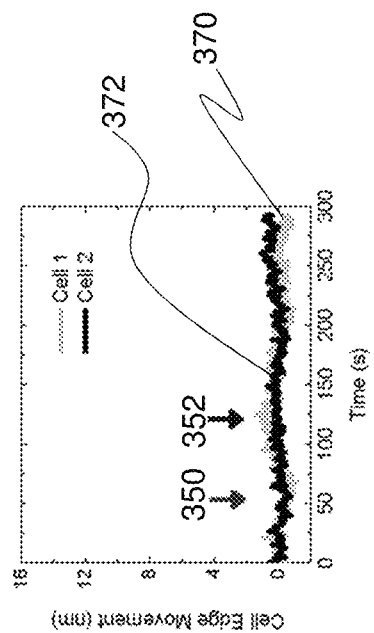
FIG. 3H represents response of wild type SH-EP1 cells to 500 nM acetylcholine.
Figure 3G:
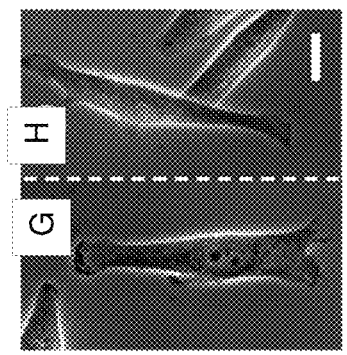
FIG. 3G illustrates phase contrast images of wild type SH-EP1 cells.

Referring now to FIG. 3G, phase contrast images of wild type SH-EP1 cells G, H are shown. The scale bar is 20 µm. As a control experiment, the measurement was carried out with wild type SH-EP1 cells, which do not have nAChRs expressed on the cell surfaces, and observed no deformation in the cell membrane. This result demonstrated that the mechanical deformation in the engineered SH-EP1 cells was indeed due to the specific binding of acetylcholine to the expressed nAChRs.

Referring now to FIG. 3H, response of wild type SH-EP1 cells to 500 nM acetylcholine is graphically shown. Arrow 350 marks the switch from 1×PBS to 500 nM acetylcholine and the arrow 352 indicates the change of solution back to 1×PBS. Curve 370 represents the measurements for cell G and lighter curve 370 represents the measurements for cell H.

Heterogeneity

Figure 4A:
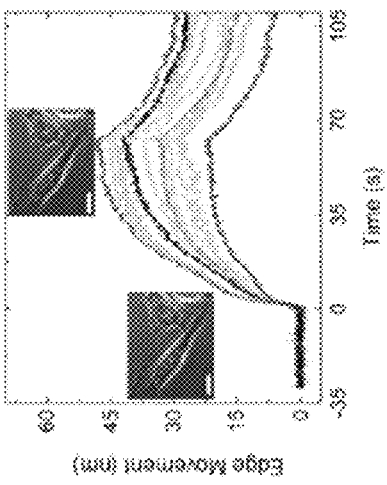
FIG. 4A and FIG. 4C show heterogeneity of small molecule interactions with cell membrane receptors. Phase contrast images of fixed human α4β2 transfected SH-EP1 cells, where the numbers mark the cells under analysis. Scale bar: 10.
Figure 4C:
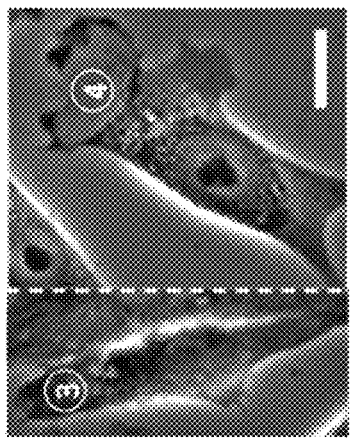
Figure 4E:
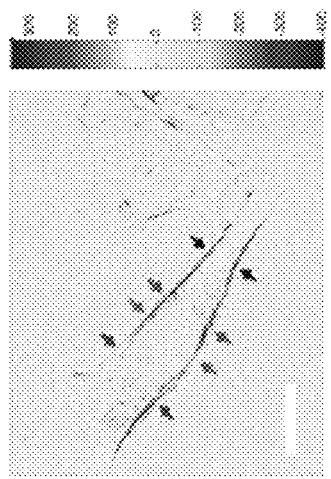
FIG. 4E graphically illustrates an example of binding kinetics at different locations (50 µM Acetylcholine).
Figure 4B:
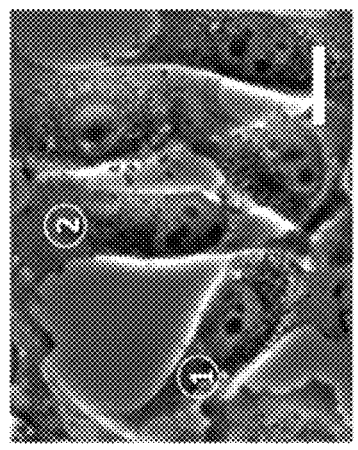
FIG. 4B graphically illustrates an example of binding kinetics of cells 1 and 2 (50 µM Acetylcholine).
Figure 4D:
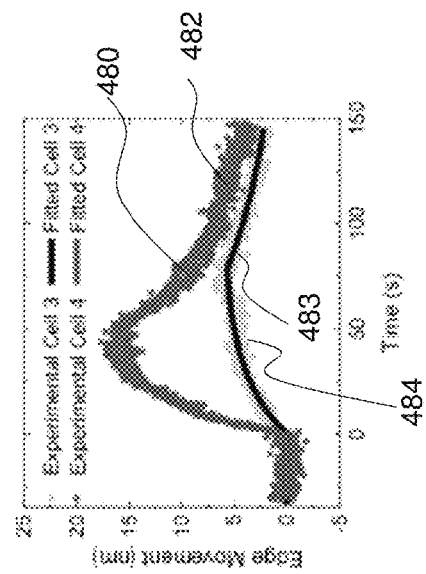
FIG. 4D graphically illustrates an example of binding kinetics of cells 3 and 4 (50 µM Acetylcholine).
Figure 4F:
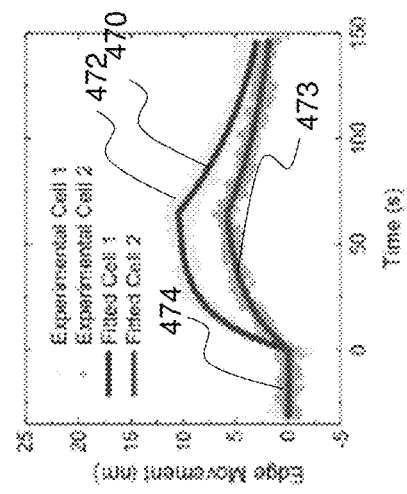
FIG. 4F shows a differential image of the cell shown in the insets of FIG. 4E obtained by subtracting the image recorded at 0 s from that at 68 s.

Referring now jointly to FIG. 4A-FIG. 4F, heterogeneity of small molecule interactions with cell membranes are illustrated. The present system makes it possible to examine the cell-cell variation and heterogeneity within a cell. FIGS. 4A and 4C are the phase contrast images of fixed SH-EP1-hα4β2 cells and numbers in circles mark the cells under analysis. The scale bar is 10 µm. Cell 1 and cell 2 are on the same glass slide, and cell 3 and cell 4 are on a different glass slide. The responses of four cells to 50-µM acetylcholine are shown in FIGS. 4B and 4D, and the corresponding kinetic constants are given in Table 1, which show significant differences in the binding kinetics. Different regions on a cell edge also show variations in the binding kinetics (FIGS. 4E and 4F). The scale bar is 10 µm. Insets 55, 65 show phase contrast images of fixed human α4β2 transfected SH-EP1 cells recorded at the time 0 s and 68 s, respectively.

Referring particularly to FIG. 4B, binding kinetics of cells 1 and 2 are graphed. The Y axis represents cell edge movement in nm and the X-axis represents time in seconds. Curve 470 represents fitted results for experimental data 472 for cell 1. Curve 473 represents fitted results for experimental data 474 for cell 2. Similarly, FIG. 4D shows binding kinetics of cells 3 and 4. The Y axis represents cell edge movement in nm and the X-axis represents time in seconds. Curve 483 represents fitted results for experimental data 484 for cell 3. Curve 480 represents fitted results for experimental data 482 for cell 4.

TABLE 1

Association rate constants ($k_{on}$), dissociation rate constants ($k_{off}$), and equilibrium constants ($K_D$) for four cells as shown in FIGS. 4A-4D.

|  | $k_{on}$ (M$^{-1}$ s$^{-1}$) | $k_{off}$ (s$^{-1}$) | $K_D$ (μM) |
| --- | --- | --- | --- |
| Cell 1 | 1.00 × 10$^3$ | 0.0152 | 15.1 |
| Cell 2 | 5.02 × 10$^2$ | 0.0139 | 28.1 |
| Cell 3 | 4.01 × 10$^2$ | 0.0142 | 36.1 |
| Cell 4 | 1.26 × 10$^3$ | 0.0150 | 11.9 |

Figure 5A:
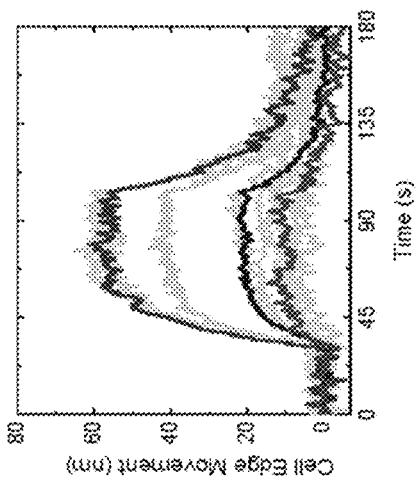
FIG. 5A and FIG. 5C show phase contrast images of fixed human α4β2 transfected SH-EP1 cells.
Figure 5B:
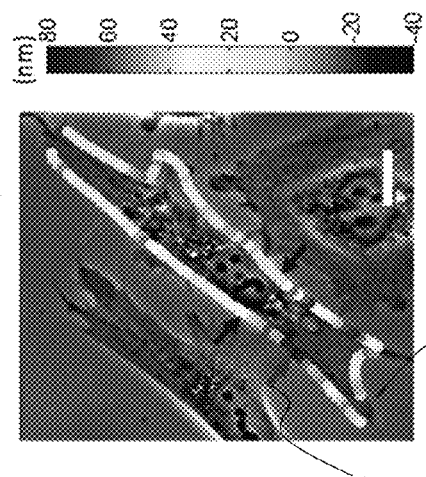
FIG. 5B and FIG. 5D graphically illustrate binding kinetics of cells.
Figure 5C:
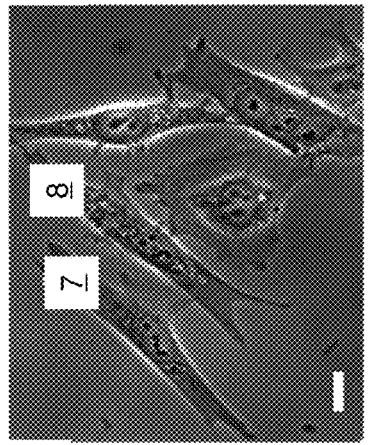

Referring now to FIG. 5A and FIG. 5C phase contrast images of fixed human α4β2 transfected SH-EP1 cells are shown. Cells under analysis include cells 5-7. The scale bars for both figures is 20 μm.

Figure 5D:
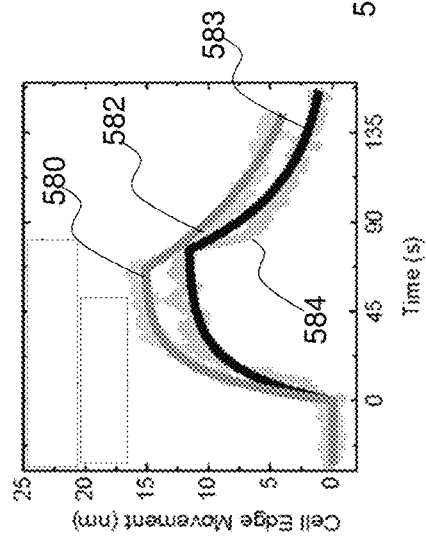

Referring to FIG. 5B, binding kinetics of cells 5 and 6 are graphed. The Y axis represents cell edge movement in nm and the X-axis represents time in seconds. Curve 570 represents fitted results for experimental data 572 for cell 5. Curve 573 represents fitted results for experimental data 574 for cell 6. Similarly, FIG. 5D shows binding kinetics of cells 7 and 8. The Y axis represents cell edge movement in nm and the X-axis represents time in seconds. Curve 583 represents fitted results for experimental data 584 for cell 7. Curve 580 represents fitted results for experimental data 582 for cell 8.

TABLE 2

Association rate constants (kon), dissociation rate constants (koff), and equilibrium constants (KD) for four cells as shown in FIG. 5A-FIG. 5D.

|  | kon (M$^{-1}$ s$^{-1}$) | koff (s$^{-1}$) | KD (nM) |
| --- | --- | --- | --- |
| Cell 5 | 7.32 × 10$^5$ | 0.0161 | 22.0 |
| Cell 6 | 8.33 × 10$^5$ | 0.0217 | 26.1 |
| Cell 7 | 3.42 × 10$^5$ | 0.0298 | 87.1 |
| Cell 8 | 5.76 × 10$^5$ | 0.0172 | 29.9 |

Figure 5E:
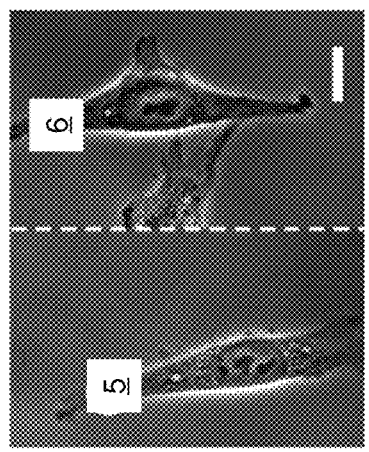
FIG. 5E graphically illustrates binding kinetics at different locations of cell in f (100 nM Acetylcholine).

Referring to FIG. 5E binding kinetics at different locations of cell (100 nM Acetylcholine) is graphically illustrated. The Y axis represents cell edge movement in nm and the X-axis represents time in seconds.

Figure 5F:
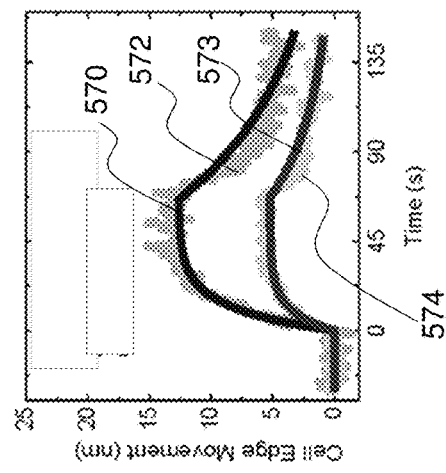
FIG. 5F shows a phase contrast image of fixed human α4β2 transfected SH-EP1 cell.

Referring to FIG. 5F, a phase contrast image of fixed human α4β2 transfected SH-EP1 cell is shown. The amount of cell membrane deformation after acetylcholine binding ranges from about 80 nm, for example, at arrow 590 to about −40 nm, at, for example, region 592 (scale bar: 20 μm).

Experimental Details

Materials

Wheat germ agglutinin (WGA) and acetylcholine chloride were purchased from Sigma-Aldrich (St. Louis, Mo.). 1× phosphate buffer saline (PBS) pH=7.4 was used as buffer for all binding experiments. All samples were prepared in 1× PBS buffer.

Cell Culture

The human α4β2 transfected human epithelial SH-EP1 cells were cultured in a humidity incubator at 37 with 5% CO2 and 70% relative humidity. Dubelco's Modified Eagle's Medium (DMEM, Lonza, Walkersville, Md.) with 10% Fetal Bovine Serum (FBS, Life Technologies, Carlsbad, Calif.) and penicillin-streptomycin (BioWhittaker, Basel, Switzerland) were used as culture medium. SH-EP1-h α4β2 cells were cultured in 25 cm$^2$ flask until approximately 80% confluence was reached for passage. 0.05% trypsin-EDTA (Life Technologies, Carlsbad, Calif.) was used for cell passage.

The CP-D cell were cultured in an incubator at 37 with 5% CO2 and 70% relative humidity. Cells were cultured in 25 cm$^2$ flask with 1× Keratinocyte-SFM (Life Technologies, Carlsbad, Calif.) and penicillin-streptomycin (BioWhittaker, Basel, Switzerland) as culture medium. When cells reached approximately 80% confluent, cells were passaged with 0.05% trypsin-EDTA (Life Technologies, Carlsbad, Calif.).

For experiments, cells were cultured overnight on the bare glass slides (22×60 mm micro cover glass, VWR, Radnor, Pa.) in a silicone well (FlexiPERM, Greiner bio-one, Monroe, N.C.) placed on top of it in order to let cells attach on the surface. Cells on glass slides were also cultured in the incubator at 37 with 5% CO2 and 70% relative humidity. Cells were incubated in 4% paraformaldehyde for 10 μmin at room temperature for fixation and then ready for experiments. Before the measurement, the small silicone well was changed to a homemade PDMS well with 2 cm in length, 1 cm in width and 1 cm in height.

High Throughput Analysis of Individual Cells with Minimized Micro-Motions

As discussed in detail above, thermodynamic principles (Eqs. 1 and 2) predict that a mechanical deformation always accompanies a molecular binding on a cell surface. This is the basic principle of MADMI. However, thermodynamics does not bring to light how much a cell will deform for a given molecular binding. This information is not needed for binding kinetic constant measurement because the kinetics constants can be determined from fitting the relative mechanical deformation vs. time plot with a kinetics model. Precise prediction of the amount of mechanical deformation associated with a binding event would require molecular scaled knowledge about the nature of the molecule-membrane protein interactions, as well as the surface density of the membrane proteins, and mechanical property of the cell. Obtaining such detailed knowledge and analyzing MADMI data in terms of the microscopic knowledge are beyond the scope of the present project. However, it is believed that the amount of mechanical deformation in MADMI increase with the binding strength and surface density of the target membrane proteins.

Figures 6A, 6B, 6C, 6D, 6E:
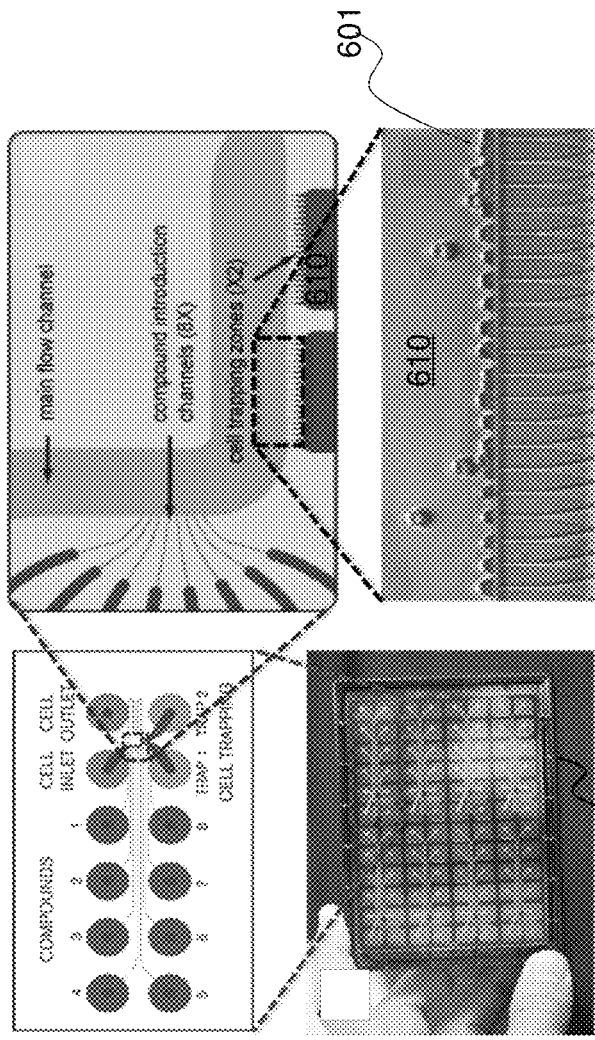
FIG. 6A-FIG. 6E schematically show a mechanism for trapping cells onto the holes of a microplate.

Referring now to FIG. 6A, trapping of cells onto the holes of a microplate is schematically shown. To minimize micromotion of live cells and achieve high throughput analysis of molecular binding kinetics, a method to trap individual cells 601 for real-time study of molecular binding kinetics of membrane proteins using MADMI will use a microplate 600 with an array of μm-scaled holes 605, such that individual cells 601 can be trapped onto the holes with an applied pressure difference across the holes. Preliminary results show that MADMI works well with adherent cells. At least one cell 601 will be trapped onto a hole 603 via a negative pressure created with a laminar flow 605 underneath the microplate 600. An objective lens 612 may be used for obtaining images. A similar method has been used in commercial automated patch clamping systems, where micron-sized holes are created in the bottom of the wells of a microplate.

Referring now jointly to FIG. 6B-FIG. 6E, apparatus for trapping cells is illustrated. FIG. 6B is a photo of a 96 well automated patch clamp plate 600 of an IonFlux Automated Patch Clamp System. FIG. 6C is an expanded view showing the fluidic design and function of each well in the IonFlux Automated Patch Clamp System of FIG. 6B. FIG. 6D is a more expanded view of a portion of the IonFlux Automated Patch Clamp System showing the cell-trapping zone 610. FIG. 6E shows an image of trapped cells. IonFlux Automated Patch Clamp Systems are available from Fluxion Biosciences, Inc., South San Francisco, Calif. 94080.

Figures 7A, 7B:
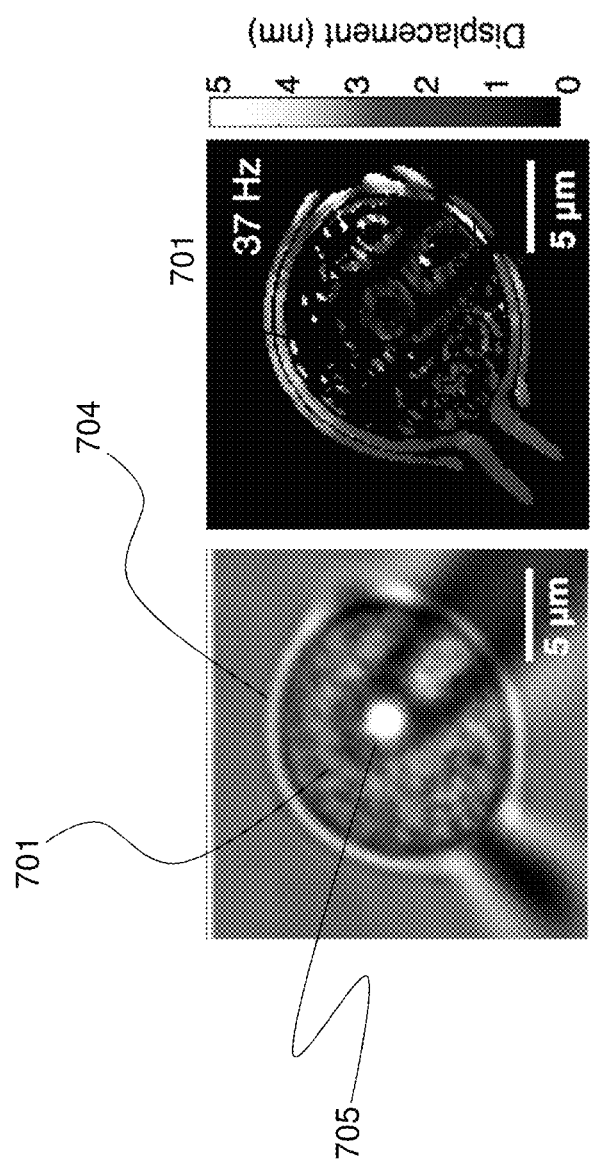
FIG. 7A shows a bright field image of a floating cell clamped with glass micropipette.
FIG. 7B shows a cell modulated by an external applied AC field.

Referring now to FIG. 7A, a bright field image of a floating cell clamped with glass micropipette is shown. A cell 701 is physically connected with micropipette 704 in a whole-cell patch configuration. The white spot 705 in the center of the cell is the tip of the micropipette. As a preliminary test to examine the feasibility of the method, a cell was trapped with a micropipette used in patch clamp. An AC electrical field having a frequency of 37 Hz was then applied across the cellular membrane to create a periodic mechanical deformation in the membrane.

Referring now to FIG. 7B, a cell 701 modulated by an external applied AC field from micropipette 704 is shown. The electromechanical coupling induced mechanical deformation was precisely measured by MADMI method and visualized with nanometer precision ranging from 0 to about 5 nm. The mechanical deformation occurred because of an electromechanical coupling effect, which was precisely measured by MADMI with nanometer precision. This preliminary test shows that it is possible to trap a cell to reduce its micro-motions, and to detect the mechanical deformation of the cell membrane with nanometer precision.

With the trapping of the cells, cellular micro-motions may be determined by performing noise spectrum analysis, and studying the micro-motions by applying different negative pressure, and effect of the size of the holes. MADMI may then be applied to determine molecular interaction kinetics using both large and small molecules, and compare the results with those of the adherent cells. Based on the finding, the cell trapping method may be optimized by tuning the diameter, flow rate and shear force for rapid cell trapping, in order to minimize the micro-motions and maximizing the throughput.

A low-noise imaging technology for studying low-density membrane proteins with MADMI. The density or abundance of the membrane proteins on cell surface varies over several orders of magnitudes ($\sim 10^3$-$10^8$ protein/cell, or 1-$10^5$ protein/$\mu m^2$). Since the binding signal is proportional to the membrane protein receptor density, in order to study low-density membrane proteins with MADMI, it is necessary to improve the detection limit of the cell membrane deformation. To achieve this goal, a low noise z-modulation Fast Fourier Transform (FFT) optical imaging technology may be used as described below. The FFT technology will periodically modulate the sample along the optical axis (z-axis) to create a periodic modulation in the focus, and determines the associated image contrast modulation with FFT, which minimizes noise and provides superior detection limit. We expect to reach a detection limit of 0.25 nm for the membrane deformation. Such a detection limit will help detect the bindings of molecules to low-density membrane proteins, e.g., 10 proteins/$\mu m^2$.

The z-modulation FFT microscope will improve the signal to noise ratio by modulating the sample stage vertically (z-axis). This is possible because the z-modulation FFT microscope will detect signals associated with the sample only, and it reduces noise from light source, optics and camera, and also removes effects due to defects or dirt in the optics of the microscope. Additionally, the periodic modulation will allow effective use of FFT filter to remove all types of noise that has different frequencies from the modulation frequency. The z-modulation microscope may advantageously be built on a traditional bright field optical microscope with an attached z-piezo modulation sample holder and proper imaging-processing algorithm. A similar method was previous demonstrated by Gineste et al.[25] An important difference is that the system disclosed herein will use periodic modulation and Fourier transform algorithm to reduce noise in the image.

The basic principle of z-modulation FFT microscopy is described by the Transport of the Intensity Equation (TIE) according to the formula $$-k\frac{\partial I(\vec{r_\perp}, 0)}{\partial z} = \nabla_\perp \cdot [I(\vec{r_\perp}, 0)\nabla_\perp \Phi(\vec{r_\perp}, 0)], k = \frac{2\pi}{\lambda} \quad (3)$$

where $I(\vec{r_\perp}, z)$ and $\phi(\vec{r_\perp}, z)$ are the intensity and phase at the position at $(\vec{r_\perp}, z)$ respectively, z denotes position along the optical axis and $\vec{r_\perp}$ denotes position within a plane normal to the optical axis, and $\lambda$ is the wavelength and k is the wavenumber. This equation relates the rate of change of intensity in the direction of the optical axis to the intensity and phase of light in a plane perpendicular to the optical axis. When $I(\vec{r_\perp}, 0)$ is constant, $I_0$, Eq. 3 can be simplified as $$\frac{\partial I(\vec{r_\perp}, 0)}{\partial z} = -\frac{I_0}{k}(\nabla_\perp^2 \Phi(\vec{r_\perp}, 0)), \quad (4)$$

where the left of the equation is the z-modulation FFT microscopy image contrast, and the right side is the spatial Laplacian, $\nabla_\perp^2$, (second derivative) of image phase, $\phi(\vec{r_\perp}, 0)$, at the focus. Eq. 4 shows that the z-modulation FFT microscopy image contrast is proportional to the second derivative of the phase of the object. For this reason, z-modulation FFT microscopy provides excellent image contrast, which allows accurate detection of the cell deformation.

Figure 8C:
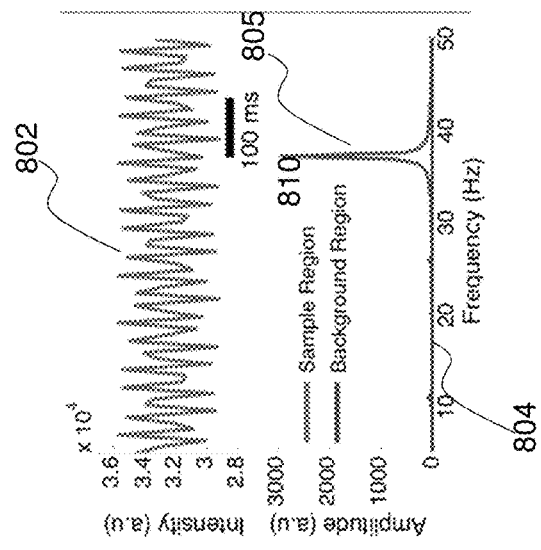
FIG. 8C schematically shows periodically modulated image intensity of a pixel, and its corresponding FFT spectrum, where a peak is located at the frequency of modulation.
Figure 8A:
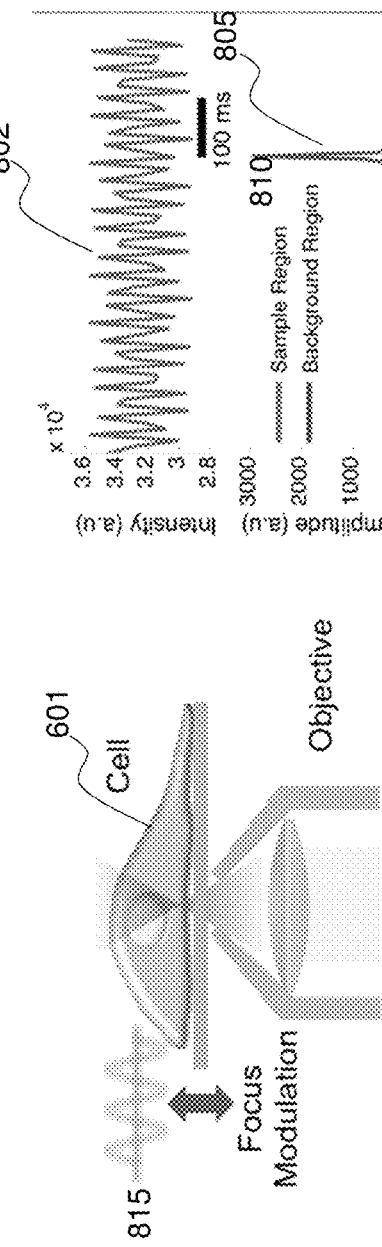
FIG. 8A schematically shows the setup of z-modulation FFT microscopy.

Referring now to FIG. 8A the setup of z-modulation FFT microscopy is shown. The sample, and thus the focal plane, is modulated vertically with a piezoelectric transducer driven by a periodic voltage 815, and bright field images are recorded sequentially.

Figure 8B:
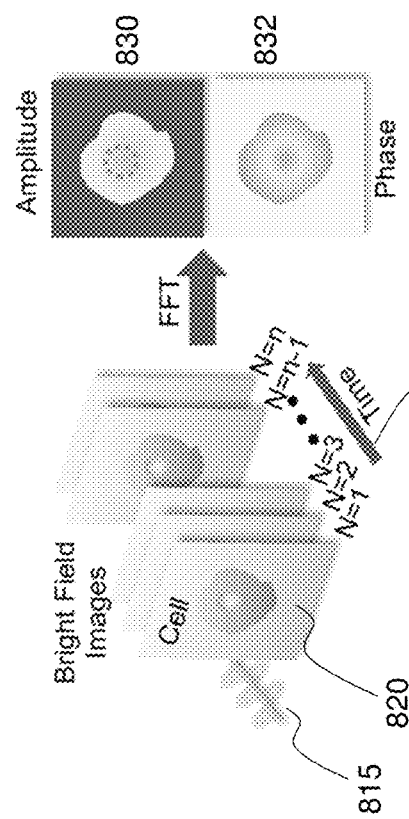
FIG. 8B schematically shows the application of temporal Fast Fourier Transform (FFT) applied to the bright field image sequences over a time window.

Referring now to FIG. 8B, to obtain the focus modulation image, temporal Fast Fourier Transform (FFT) was applied to the bright field image sequences 820 over a time window 822. Amplitude data 830 and phase data 832 can thus be obtained.

Referring now to FIG. 8C, a periodically modulated image intensity of a pixel, and its corresponding FFT spectrum, where a peak is located at the frequency of modulation are shown. Plot 802 is a time plot of modulated image intensity. FFT intensity spectrum for a background region 804 and a sample region 805 with focus modulation at 37 Hz is shown. A peak 810 appears in the FFT spectrum at the modulation frequency for the sample region, but not in the background region. The amplitude of the peak 810 was extracted for each pixel to create a z-modulation FFT microscopy image.

Figure 8F:
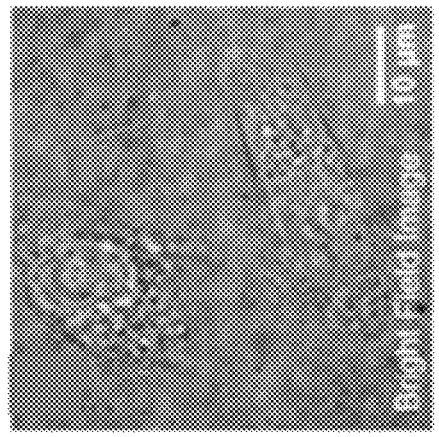
FIG. 8F and FIG. 8G contrast a z-modulation FFT image showing superior contrast compared with the traditional bright field image obtained with same camera.
Figure 8G:
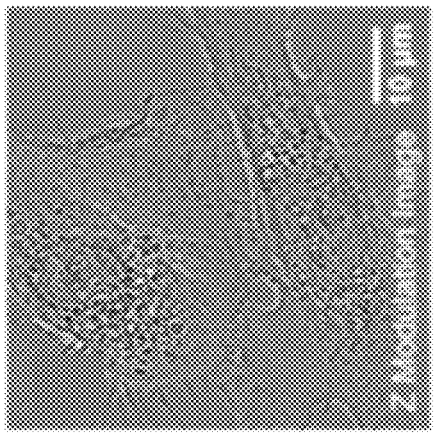
Figure 8D:
FIG. 8D and FIG. 8E illustrate individual 42 nm polystyrene nanoparticles that are invisible in bright field image, but are clearly visible in the modulation image.
Figure 8E:
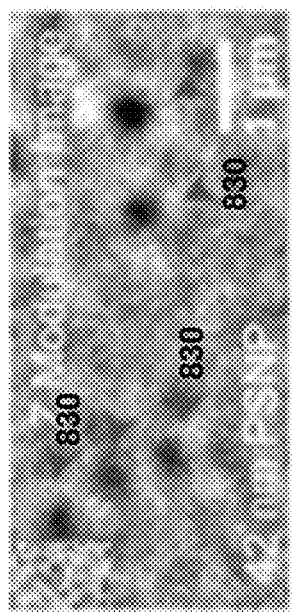

Referring now jointly to FIG. 8D and FIG. 8E, to evaluate noise reduction capability of z-modulation FFT microscopy, 42 nm polystyrene nanoparticle (PSNP) were imaged on a glass surface. Individual 42 nm polystyrene nanoparticles are invisible in bright field image (FIG. 8D), but are clearly visible in the modulation image as marked by arrows 830 (FIG. 8E). Similarly, background noise in the bright field image (FIG. 8D) of cells is removed (FIG. 8G) and detailed cellular structures are enhanced in the z-modulation FFT image. FIG. 8D shows the traditional bright field image of the same sample, which cannot resolve the nanoparticles due to noise. In contrast, z-modulation FFT microscopy can clearly resolve individual 42 nm PSNPs, as shown in FIG. 8E. Another example is cultured cells. The z-modulation FFT image (FIG. 8G) shows superior contrast compared with the traditional bright field image obtained with same camera (FIG. 8F). Individual 42 nm polystyrene nanoparticles are invisible in bright field image (FIG. 8D), but are clearly visible in the modulation image as marked by arrows 830 (FIG. 8E). Similarly, background noise in the bright field image (FIG. 8D) of cells is removed (FIG. 8G) and detailed cellular structures are enhanced in the z-modulation FFT image.

Figure 9C:
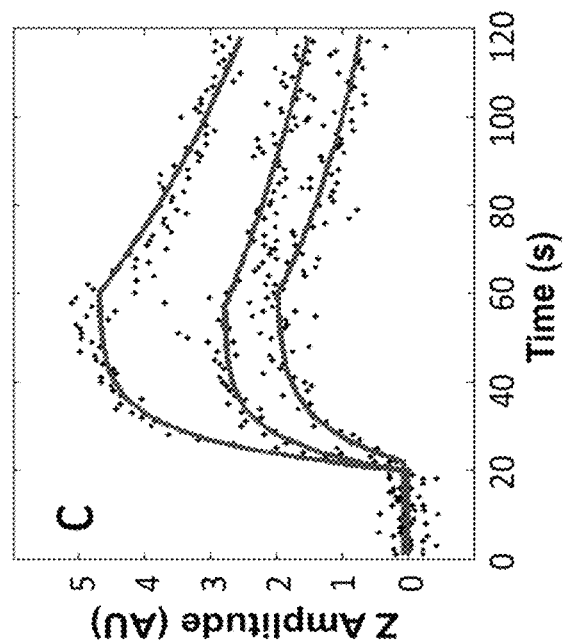
FIG. 9C illustrates binding kinetic plots of 10, 20 and 50 µg/ml WGA.
Figure 9A:
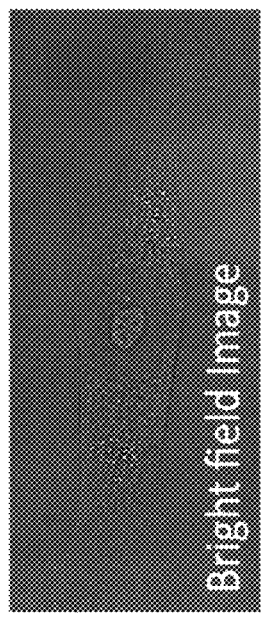
FIG. 9A and FIG. 9B show images from a preliminary test of WGA binding kinetics on a SHEP1 cell with the z-modulation FFT microscope are shown.
Figure 9B:
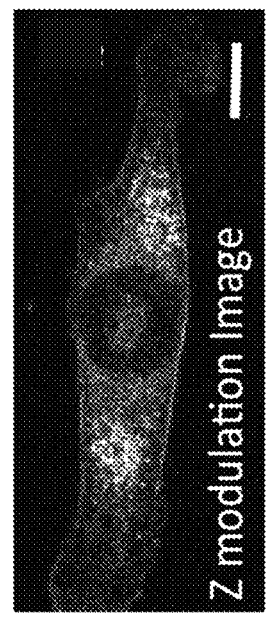

Referring now jointly to FIG. 9A and FIG. 9B, images from a preliminary test of WGA binding kinetics on a SHEP1 cell with the z-modulation FFT microscope are shown. FIG. 9. WGA binding kinetic measured by z-modulation FFT microscopy. FIG. 9A Bright field image of fixed SHEP1 cell; FIG. 9B z-modulation FFT image of the same cell; FIG. 9C Binding kinetic plots of 10, 20 and 50 μg/ml WGA (from bottom to top curves). The plots were obtained by tracking the intensity changes along the edge of the modulation amplitude image. Measured kinetic constants: $k_{on}=1.4\times10^4 M^{-1} s^{-1}$, $k_{off}=0.013 s^{-1}$, $K_D=125$ nM. Scale bar: 10 μm. The kinetic curves were obtained from the amplitude of the image sequences along the edge of a cell. Kinetic constants and binding affinity were obtained by fitting the kinetic curves with first order kinetic model.

The z-modulation FFT imaging technology together with the differential optical algorithm may be used to study molecular binding kinetics of membrane proteins with different expression levels. One of the model systems planned for study is human epidermal growth factor receptor (EGFR, or HER1), which interacts with target protein drug, Panitumumab (Vectibix, FDA approved recombinant human IgG2k mAb drug manufactured by Amgen). EGFR plays an essential role in regulating normal cell signaling, and the mutation of EGFR leads to cell proliferation, angiogenesis, invasion, metastasis and inhibition of apoptosis, accounting for the pathogenesis and progression of cancer cells (33-37). Monoclonal antibodies targeting the extracellular do-main of EGFR have been used in various stages of pre-clinical development, and have shown good therapeutic efficacy for treatment of a number of cancers that have up-regulated EGFR expression level. The kinetic constants of the binding of these antibody drugs to EGFR receptors are the key parameters to characterize the efficacy of these drugs. We will use cell lines with different EGFR expression levels to measure the antibody drug interaction kinetics, and to evaluate the detection limit of MADMI.

Cell lines with different expression levels of EGFR, including A431 (high), Hela (medium) and A549 (low), and HEK293 (negative control) will be used. The EGFR expression levels of these cells have been confirmed in our lab using quantitative SPR imaging and immunofluorescence imaging. The membrane densities of EGFR in A431, Hela and A549 cells calculated from maximum SPR binding signals are 640, 270 and 140 receptors/$\mu m^2$, respectively.

Binding kinetic curves of different doses of Panitumumab antibody with these four cell lines will be measured by MADMI. Kinetic constants will be obtained through globe fitting of the binding kinetics curves, and EGFR expression level will be quantified from the maximum binding signal.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

The following publications are incorporated by reference.
1. Ehrlich, P. Address in pathology on chemotherapeutics: Scientific principles, methods, and results. 2, 445-451 (1913).
2. Copeland, R. A., Pompliano, D. L. & Meek, T. D. Opinion—Drug-target residence time and its implications for lead optimization. *Nature Rev. Drug Disc.* 5, 730-739 (2006).
3. Swinney, D. C. The role of binding kinetics in therapeutically useful drug action. *Curr. Opin. Drug Disc. Develop.* 12, 31-39 (2009).
4. Ernst, R. E., High, K. N., Glass, T. R. & Zhao, Q. in *Therapeutic Monoclonal Antibodies: From Bench to Clinic* (ed Zhiqiang An) (John Wiley & Sons, Inc., 2009).
5. Butcher, E. C. Can cell systems biology rescue drug discovery? *Nature Rev. Drug Disc.* 4, 461-467 (2005).
6. Hopkins, A. L. & Groom, C. R. The druggable genome. *Nature Rev. Drug Disc.* 1, 727-730 (2002).
7. Nahta, R. & Esteva, F. J. Herceptin: mechanisms of action and resistance. *Cancer Lett.* 232, 123-138 (2006).
8. Nahta, R., Yu, D. H., Hung, M. C., Hortobagyi, G. N. & Esteva, F. J. Mechanisms of disease: understanding resistance to HER2-targeted therapy in human breast cancer. *Nat. Clin. Pract. Oncol.* 3, 269-280 (2006).
9. Valabrega, G., Montemurro, F. & Aglietta, M. Trastuzumab: mechanism of action, resistance and future perspectives in HER2-overexpressing breast cancer. *Annal. Oncol.* 18, 977-984 (2007).
10. Nagy, P. et al. Decreased accessibility and lack of activation of ErbB2 in JIMT-1, a herceptin-resistant, MUC4-Expressing breast cancer cell line. *Cancer Res.* 65, 473-482 (2005).
11. Price-Schiavi, S. A. et al. Rat MUC4 (sialomucin complex) reduces binding of anti-ErbB2 antibodies to tumor cell surfaces, a potential mechanism for Herceptin resistance. *Int. J. Cancer* 99, 783-791 (2002).
12. Kute, T. et al. Development of Herceptin resistance in breast cancer cells. *Cyto. Part A* 57A, 86-93 (2004).
13. Lu, Y. H., Zi, X. L., Zhao, Y. H., Mascarenhas, D. & Pollak, M. Insulin-like growth factor-I receptor signaling and resistance to trastuzumab (Herceptin). *J. Natl. Cancer Inst.* 93, 1852-1857 (2001).
14. Nahta, R., Takahashi, T., Ueno, N. T., Hung, M. C. & Esteva, F. J. P27(kip1) down-regulation is associated with trastuzumab resistance in breast cancer cells. *Cancer Res.* 64, 3981-3986 (2004).

15. Darling, R. J. & Brault, P. A. Kinetic exclusion assay technology: Characterization of molecular interactions. *Assay Drug Develop. Technol.* 2, 647-657 (2004).
16. Xie, L. et al. Measurement of the functional affinity constant of a monoclonal antibody for cell surface receptors using kinetic exclusion fluorescence immunoassay. *J. Immuno. Methods* 304, 1-14 (2005).
17. Rathanaswami, P., Babcook, J. & Gallo, M. High-affinity binding measurements of antibodies to cell-surface-expressed antigens. *Anal. Biochem.* 373, 52-60 (2008).
18. Pei, Z. C., Saint-Guirons, J., Kack, C., Ingemarsson, B. & Aastrup, T. Real-time analysis of the carbohydrates on cell surfaces using a QCM biosensor: a lectin-based approach. *Biosen. Bioelectron.* 35, 200-205 (2012).
19. Wang, W. et al. Label-free measuring and mapping of binding kinetics of membrane proteins in single living cells. *Nature Chem.* 4, 846-853 (2012).
20. Troise, F., Cafaro, V., Giancola, C., D'Alessio, G. & De Lorenzo, C. Differential binding of human immunoagents and Herceptin to the ErbB2 receptor. *FEBS J.* 275, 4967-4979 (2008).
21. Pan, A. C., Borhani, D. W., Dror, R. O. & Shaw, D. E. Molecular determinants of drug-receptor binding kinetics. *Drug Disc. Today* in press (2013).
22. DeFazio-Eli, L. et al. Quantitative assays for the measurement of HER1-HER2 heterodimerization and phosphorylation in cell lines and breast tumors: applications for diagnostics and targeted drug mechanism of action. *Breast Cancer Res.* 13 (2011).
23. Pearlberg, J. et al. Screens using RNAi and cDNA expression as surrogates for genetics in mammalian tissue culture cells. *Cold Spring Harb. Symp. Quant. Biol.* 70, 449-459 (2005).
24. Hathaway, H. J. et al. Detection of breast cancer cells using targeted magnetic nanoparticles and ultra-sensitive magnetic field sensors. *Breast Cancer Res.* 13 (2011).
25. Gineste J M, Macko P, Patterson E A, Whelan M P. Three-dimensional automated nanoparticle tracking using Mie scattering in an optical microscope. J Microsc-Oxford. 2011; 243(2):172-8. doi: DOI 10.1111/j.1365-2818.2011.03491.x. PubMed PMID: WOS:000292845200006.

What is claimed is:

1. A system for quantitative detection and analysis of the binding of molecules with molecular receptors on the surfaces of a biological object, the system comprising:
   a microscope positioned to image the biological object and transmit a time sequence of images of the biological object;
   a camera located to receive the transmitted time sequence of images of the biological object from the microscope and transmit data representing the time sequence of images;
   a plurality of molecules introduced to bind with the molecular receptors;
   a processor, coupled to receive the data representing the time sequence of images from the camera;
   the processor including an image processing algorithm that quantitatively determines mechanical deformation of the biological object from the time sequence of images, wherein the mechanical deformation is due to an interaction of the biological object with the plurality of molecules, wherein the image processing algorithm determines mechanical deformation by using an edge detector to determine an edge of the biological object and a time sequence tracker for tracking a plurality of movements of the edge by measuring positions of the edge at different times, and
   wherein the image processing algorithm also determines molecular binding kinetic values of the biological object as proportional to the mechanical deformation of the biological object.

2. The system of claim 1 wherein the time sequence tracker for tracking the plurality of movements of the edge of the biological object comprises a differential image intensity analysis algorithm.

3. The system of claim 1 wherein the biological object comprises a biological cell, tissue or virus.

4. The system of claim 1 wherein the plurality of molecules are selected from the group consisting of proteins, nucleic acids, amino acids, peptides, hormones, drugs, metabolites, minerals, and ions.

5. The system of claim 1 wherein the microscope comprises an optical microscope.

6. The system of claim 5 wherein the optical microscope comprises a phase contrast microscope.

7. The system of claim 1 wherein the biological object comprises a neuron and the plurality of molecules comprise neuron stimulator molecules that stimulate an electrical activity of the neuron.

8. The system of claim 7 wherein the neuron stimulator molecules comprise agonists or antagonists.

9. The system of claim 1 wherein the microscope comprises a z-modulation temporal Fast Fourier Transform (FFT) microscope.

10. The system of claim 1 wherein the biological object is a cell and the image processor operates to measure the plurality of movements of the edge of the biological object by: detecting a cell edge from an optical image of the cell; selecting a region of interest (ROI) at a location of the cell edge; dividing the ROI into two equal halves, wherein one half is inside of the cell, and wherein the second half falls outside of the cell; and determining the edge movement by computing (A−B)/(A+B), where A and B are the intensities of the two halves of the image.

11. A method for quantitative detection and analysis of the binding of molecules with molecular receptors on the surfaces of a biological object, the method comprising:
   operating a microscope and a sensor to capture a time sequence of images of a biological object;
   introducing a plurality of molecules to interact with the biological object;
   operating a processor to quantitatively determine the mechanical deformation of the biological object from the time sequence of images due to interaction of the biological object with the plurality of molecules, wherein determining the mechanical deformation comprises operating an edge detector for determining an edge of the biological object and tracking a plurality of movements of the edge by measuring positions of the edge at different times; and
   operating the processor to determine molecular binding kinetic values of the biological object as proportional to the mechanical deformation of the biological object and to determine binding kinetic constants, including ka, kd and KD from the time sequence of images.

12. The system of claim 11 wherein tracking the plurality of movements of the edge of the biological object further comprises running a differential image intensity analysis algorithm on the processor.

13. The method of claim 11 wherein the biological object comprises a biological cell, tissue or virus.

14. The method of claim 11 wherein the plurality of molecules are selected from the group consisting of proteins, nucleic acids, amino acids, peptides, hormones, drugs, metabolites, minerals, and ions.

15. The method of claim 11 wherein the microscope comprises an optical microscope and the sensor comprises a MOS imager or CCD imager.

16. The method of claim 15 wherein the optical microscope comprises a phase contrast microscope.

17. The method of claim 11 wherein the biological object comprises a neuron and the plurality of molecules comprise neuron stimulator or inhibitor molecules that stimulate or inhibit electrical activity of the neuron.

18. The method of claim 17 wherein the neuron stimulator molecules comprise agonists or antagonists.

19. The method of claim 11 wherein the microscope comprises a z-modulation temporal Fast Fourier Transform (FFT) microscope to produce images.

20. A system for quantitative detection and analysis of binding of neuron stimulator molecules with molecular receptors on the surfaces of a neuron, the system comprising:
- a microscope positioned to image the neuron and transmit a time sequence of images of the biological object;
- an image sensor located to receive transmitted images of the neuron from the microscope and transmit data representing the time sequence of images;
- neuron stimulator molecules introduced to bind with the molecular receptors;
- a processor coupled to receive the data representing the time sequence of images from the image sensor, the processor including an image processing algorithm that quantitatively determines mechanical deformation of the neuron from the time sequence of images, wherein the mechanical deformation is due to interaction of the neuron with the plurality of neuron stimulator molecules, wherein the image processing algorithm determines mechanical deformation by using an edge detector to determine an edge of the biological object and a time sequence tracker for tracking a plurality of movements of the edge by measuring positions of the edge at different times, and
- wherein the image processing algorithm also determines molecular binding kinetic values of the neuron as proportional to the mechanical deformation of the neuron.

21. The system of claim 20 wherein the neuron stimulator molecules comprise nicotinic acetylcholine receptors.

22. A method for quantitative detection and analysis of the binding of neuron stimulator molecules with molecular receptors on the surfaces of a neuron, the method comprising:
- operating a microscope and a sensor to capture a time sequence of images of a biological object;
- introducing a plurality of neuron stimulator molecules to interact with the neuron;
- operating a processor to quantitatively determine mechanical deformation of the neuron from the time sequence of images due to interaction of the neuron with the plurality of neuron stimulator molecules, wherein determining the mechanical deformation comprises operating an edge detector for determining an edge of the biological object and tracking a plurality of movements of the edge by measuring positions of the edge at different times; and
- operating the processor to determine molecular binding kinetic values of the neuron as proportional to the mechanical deformation of the neuron.

23. The method of claim 22 wherein the neuron stimulator molecules comprise nicotinic acetylcholine receptors.

* * * * *